(12) United States Patent
Younis et al.

(10) Patent No.: US 9,266,842 B2
(45) Date of Patent: Feb. 23, 2016

(54) ANTI-MALARIAL AGENTS

(71) Applicants: UNIVERSITY OF CAPE TOWN, Rondebosch (ZA); MMV MEDICINES FOR MALARIA VENTURE, Geneva (CH)

(72) Inventors: Yassir Younis, Capetown (ZA); Kelly Chibale, Claremont (ZA); Michael John Witty, Dover (GB); David Waterson, Nyon (CH)

(73) Assignees: MMV MEDICINES FOR MALARIA VENTURE, Geneva (CH); UNIVERSITY OF CAPE TOWN, Rondebosch (ZA)

( * ) Notice: Subject to any disclaimer, the term of this patent is extended or adjusted under 35 U.S.C. 154(b) by 0 days.

(21) Appl. No.: 14/379,332

(22) PCT Filed: Feb. 15, 2013

(86) PCT No.: PCT/IB2013/051235
§ 371 (c)(1),
(2) Date: Aug. 18, 2014

(87) PCT Pub. No.: WO2013/121387
PCT Pub. Date: Aug. 22, 2013

(65) Prior Publication Data
US 2015/0031682 A1    Jan. 29, 2015

Related U.S. Application Data

(60) Provisional application No. 61/600,234, filed on Feb. 17, 2012.

(51) Int. Cl.
| | |
|---|---|
| *A61K 31/497* | (2006.01) |
| *A61K 31/4965* | (2006.01) |
| *C07D 241/20* | (2006.01) |
| *C07D 401/04* | (2006.01) |
| *C07D 401/14* | (2006.01) |
| *C07D 403/10* | (2006.01) |
| *C07D 401/10* | (2006.01) |
| *A61K 31/551* | (2006.01) |
| *A61K 31/5377* | (2006.01) |
| *A61K 45/06* | (2006.01) |

(52) U.S. Cl.
CPC ............ *C07D 241/20* (2013.01); *A61K 31/497* (2013.01); *A61K 31/4965* (2013.01); *A61K 31/5377* (2013.01); *A61K 31/551* (2013.01); *A61K 45/06* (2013.01); *C07D 401/04* (2013.01); *C07D 401/10* (2013.01); *C07D 401/14* (2013.01); *C07D 403/10* (2013.01)

(58) Field of Classification Search
CPC .. C07D 241/20; C07D 401/04; C07D 401/14; C07D 403/10
See application file for complete search history.

(56) References Cited

U.S. PATENT DOCUMENTS

2012/0225857 A1    9/2012  Augeri et al.

FOREIGN PATENT DOCUMENTS

| WO | WO 2007/147874 | 12/2007 |
| WO | WO 2008/074997 | 6/2008 |
| WO | WO 2011/086531 | 7/2011 |

OTHER PUBLICATIONS

Fidock, D. A. et al. "Antimalarial drug discovery: Efficacy models for compound screening" *Nature Reviews*, Jun. 1, 2004, pp. 509-520, vol. 3, No. 6.
Miyaura, N. et al. "Palladium-Catalyzed Cross-Coupling Reactions of Organoboron Compounds" *Chem. Rev.*, 1995, pp. 2457-2483, vol. 95.
Younis, Y. et al. "Cell-Based Medicinal Chemistry Optimization of High Throughput Screening Hits for Orally Active Antimalarials. Part 2: Hits from SoftFocus Kinase and other Libraries" *Journal of Medicinal Chemistry*, 2013, pp. 7750-7754, vol. 56.
Written Opinion in International Application No. PCT/IB2013/051235, Jun. 13, 2013, pp. 1-7.
Younis, Y. et al. "Structure-Activity-Relationship Studies around the 2-Amino Group and Pyridine Core of Antimalarial 3,5-Diarylaminopyridines Lead to a Novel Series of Pyrazine Analogues with Oral in Vivo Activity" *Journal of Medicinal Chemistry, 2013*, pp. 8860-8871, vol. 56, No. 21.

*Primary Examiner* — Brian McDowell
(74) *Attorney, Agent, or Firm* — Saliwanchik, Lloyd & Eisenschenk

(57) ABSTRACT

The present invention is related to a use of aminopyrazine derivatives in the manufacture of a medicament for preventing or treating malaria. Specifically, the present invention is related to aminopyrazine derivatives useful for the preparation of a pharmaceutical formulation for the inhibition of malaria parasite proliferation. In one embodiment, the invention provides aminopyrazine derivatives having the following formula:

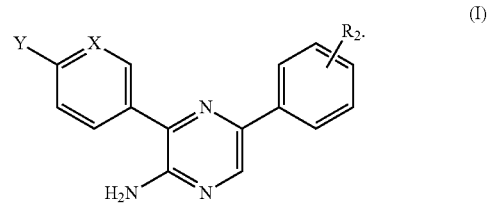

(I)

20 Claims, No Drawings

ANTI-MALARIAL AGENTS

CROSS-REFERENCE TO RELATED APPLICATIONS

This application is the U.S. national stage application of International Patent Application No. PCT/IB2013/051235, filed Feb. 15, 2013, which claims the benefit of U.S. Provisional Patent Application No. 61/600,324, filed Feb. 17, 2012.

FIELD OF THE INVENTION

The present invention relates to novel anti-malarial agents. Specifically, the present invention is related to agents useful for the preparation of a pharmaceutical formulation for preventing or treating malaria and methods of their use and manufacture.

BACKGROUND OF THE INVENTION

Malaria is caused by protozoan parasites of the genus *Plasmodium* that infect and destroy red blood cells, leading to fever, severe anemia, cerebral malaria and, if untreated, death. *Plasmodium falciparum* is the dominant species in sub-Saharan Africa, and is responsible for the almost 1 million deaths each year. The disease burden is heaviest in African children under 5 years of age and in pregnant women. *Plasmodium vivax* causes 25-40% of the global malaria burden, particularly in South and Southeast Asia, and Central and South America. The other two main species that are known to infect humans are *Plasmodium ovale* and *Plasmodium malariae*.

Malaria is a disease that is prevalent in many developing countries. Approximately 40% of the world's population lives in countries where the disease is endemic; approximately 247 million people suffer from the disease every year.

Various medications are presently used for the treatment of malaria. However, many of these medications are costly and some exhibit significant toxicity and undesirable side effects in humans. Drugs used for treating malaria include artemisinin and its derivatives, chloroquine, quinine, mefloquine, amodiaquine, atovaquone/proguanil, doxycycline, hydroxychloroquine, halofantrine, pyrimethamine-sulfadoxine, and primaquine.

However, the widespread emergence of drug resistance of malaria parasites in many tropical countries has compromised many of the current chemotherapies and there is a continued need for new chemotherapeutic approaches. Accordingly, this invention provides novel potent anti-malarial agents and methodology of treating malaria using novel potent anti-malarial agents.

SUMMARY OF THE INVENTION

The present invention is directed towards novel aminopyrazine derivatives which are useful in the treatment and/or prophylaxis of malaria, pharmaceutical formulation, use and manufacture thereof.

A first aspect of the invention provides an aminopyrazine derivative according to the invention or a pharmaceutically acceptable salt thereof or a pharmaceutically active derivative thereof.

A second aspect of the invention relates to an aminopyrazine derivative or a pharmaceutically acceptable salt thereof or a pharmaceutically active derivative thereof according to the invention for use as a medicament.

A third aspect of the invention relates to the use of an aminopyrazine derivative according to the invention or a pharmaceutically acceptable salt thereof or a pharmaceutically active derivative thereof, for the preparation of a pharmaceutical composition for the prevention and/or treatment of malaria.

A fourth aspect of the invention resides in a pharmaceutical formulation comprising at least one aminopyrazine derivative according to the invention or a pharmaceutically acceptable salt thereof or a pharmaceutically active derivative thereof, and a pharmaceutically acceptable carrier, diluent or excipient thereof.

A fifth aspect of the invention relates to an aminopyrazine derivative according to the invention or a pharmaceutically acceptable salt thereof or a pharmaceutically active derivative thereof, for use in the prevention and/or treatment of malaria.

A sixth aspect of the invention resides in a method for preventing and/or treating malaria in a patient. The method comprises administering an aminopyrazine derivative according to the invention or a pharmaceutically acceptable salt thereof or a pharmaceutically active derivative thereof in a patient in need thereof.

A seventh aspect of the invention provides a process for the preparation of an aminopyrazine derivative according to the invention or a pharmaceutically acceptable salt thereof or a pharmaceutically active derivative thereof according to the invention and intermediates thereof.

An eighth aspect of the invention provides an intermediate of formula (v) according to the invention.

A ninth provides an intermediate of formula (viii) according to the invention.

A tenth aspect provides an intermediate of formula (ix) according to the invention.

An eleventh aspect provides a process for the preparation of a compound of Formula (I) comprising a step of reacting an intermediate of formula (v).

A twelfth aspect provides a process for the preparation of a compound of Formula (I) comprising a step of reacting an intermediate of formula (viii).

A thirteenth aspect provides a process for the preparation of a compound of Formula (I) comprising a step of reacting an intermediate of formula (xix).

A fourteenth aspect provides intermediates useful in the preparation of a compound of Formula (I) and processes for the preparation thereof.

Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "$C_1$-$C_6$ alkyl" when used alone or in combination with other terms, comprises a straight chain or branched $C_1$-$C_6$ alkyl which refers to monovalent alkyl groups having 1 to 6 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, methylbutyl, 2,2-dimethylpropyl, n-hexyl, 2-methylpentyl, 3-methylpentyl, 4-methylpentyl, and the like.

The term "$C_2$-$C_6$ alkenyl" when used alone or in combination with other terms, comprises a straight chain or branched $C_2$-$C_6$ alkenyl. Particularly, it refers to groups having 2 to 6 carbon atoms and having at least 1 or 2 sites of alkenyl unsaturation. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, and the like. Among others, are vinyl or ethenyl (—CH=CH$_2$), n-2-propenyl (allyl, —CH$_2$CH=CH$_2$), isopropenyl, 1-propenyl, 2-methyl-1-propenyl, 1-butenyl, 2-butenyl, and 3-methyl-2-butenyl and the like.

The term "$C_2$-$C_6$ alkynyl" when used alone or in combination with other terms, comprises a straight chain or branched $C_2$-$C_6$ alkynyl. It may have any available number of triple bonds in any available positions. This term is exemplified by groups such as alkynyl groups that may have a carbon number of 2-6, and optionally a double bond, such as ethynyl (—C≡CH), 1-propynyl, 2-propynyl (propargyl: —CH$_2$C≡CH), 2-butynyl, 2-pentene-4-ynyl, and the like.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "aryl" refers to an unsaturated aromatic carbocyclic group of from 6 to 14 carbon atoms having a single ring (e.g. phenyl) or multiple condensed rings (e.g., indenyl, naphthyl). Aryl include phenyl, naphthyl, anthryl, phenanthrenyl and the like.

The term "$C_1$-$C_6$ alkyl aryl" refers to aryl groups having a $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, isoquinolinyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "$C_1$-$C_6$ alkyl heteroaryl" refers to heteroaryl groups having a $C_1$-$C_6$ alkyl substituent, including methyl furyl and the like.

The term "heteroaryl $C_1$-$C_6$ alkyl" refers to $C_1$-$C_6$ alkyl groups having a heteroaryl substituent, including furyl methyl and the like.

The term "$C_2$-$C_6$ alkenyl aryl" refers to an aryl groups having a $C_2$-$C_6$ alkenyl substituent, including vinyl phenyl and the like.

The term "aryl $C_2$-$C_6$ alkenyl" refers to a $C_2$-$C_6$ alkenyl groups having an aryl substituent, including phenyl vinyl and the like.

The term "$C_2$-$C_6$ alkenyl heteroaryl" refers to heteroaryl groups having a $C_2$-$C_6$ alkenyl substituent, including vinyl pyridinyl and the like.

The term "heteroaryl $C_2$-$C_6$ alkenyl" refers to $C_2$-$C_6$ alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g. cyclohexyl) or multiple condensed rings (e.g. norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl.

Heterocycloalkyl include pyrrolidinyl, piperidinyl, piperazinyl, morpholinyl, tetrahydrofuranyl and the like.

The term "$C_1$-$C_6$ alkyl $C_3$-$C_8$-cycloalkyl" refers to $C_3$-$C_8$-cycloalkyl groups having a $C_1$-$C_6$ alkyl substituent, including methyl cyclopentyl and the like.

The term "$C_3$-$C_8$-cycloalkyl $C_1$-$C_6$ alkyl" refers to $C_1$-$C_6$ alkyl groups having a $C_3$-$C_8$-cycloalkyl substituent, including 3-cyclopentyl propyl and the like.

The term "$C_1$-$C_6$ alkyl heterocycloalkyl" refers to heterocycloalkyl groups having a $C_1$-$C_6$ alkyl substituent, including 4-methylpiperidinyl and the like.

The term "heterocycloalkyl $C_1$-$C_6$ alkyl" refers to $C_1$-$C_6$ alkyl groups having a heterocycloalkyl substituent, including (1-methylpiperidin-4-yl) methyl and the like.

The term "carboxy" refers to the group —C(O)OH.

The term "carboxy $C_1$-$C_6$ alkyl" refers to $C_1$-$C_6$ alkyl groups having a carboxy substituent, including 2-carboxyethyl and the like.

The term "acyl" refers to the group —C(O)R where R includes H, "$C_1$-$C_6$ alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "$C_1$-$C_6$ alkyl", "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetyloxy and the like.

The term "acyloxy $C_1$-$C_6$ alkyl" refers to alkyl groups having an acyloxy substituent, including 2-(ethylcarbonyloxy)ethyl and the like.

The term "alkoxy" refers to the group —O—R where R includes optionally substituted "$C_1$-$C_6$ alkyl", optionally substituted "aryl", optionally substituted "heteroaryl", optionally substituted "aryl $C_1$-$C_6$ alkyl" or optionally substituted "heteroaryl $C_1$-$C_6$ alkyl".

The term "alkoxy $C_1$-$C_6$ alkyl" refers to $C_1$-$C_6$ alkyl groups having an alkoxy substituent, including methoxyethyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to $C_1$-$C_6$ alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "ureido" refers to the group —NRC(O)NR'R" where R, R and R" are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_2$-$C_6$ alkyl," or "heterocycloalkyl $C_1$-$C_6$ alkyl," and where R' and R," together with the nitrogen atom to which they are attached, can optionally form a 3-8-membered heterocycloalkyl ring.

The term "ureido $C_1$-$C_6$ alkyl" refers to $C_1$-$C_6$-alkyl groups having an ureido substituent, including 2-(N'-methylureido)ethyl and the like.

The term "carbamate" refers to the group —NRC(O)OR' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "$C_1$-$C_6$ alkyl aryl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl" and optionally R can also be hydrogen.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl heteroaryl", "$C_3$-$C_8$-cycloalkyl," or "heterocycloalkyl," and where R and R', together with the nitrogen atom to which they are attached, can optionally form a 3-8-membered heterocycloalkyl ring.

The term "amino $C_1$-$C_6$ alkyl" refers to alkyl groups having an amino substituent, including 2-(1-pyrrolidinyl)ethyl and the like.

The term "ammonium" refers to a positively charged group —N$^+$RR'R" where R, R' and R" are independently "$C_1$-$C_6$ alkyl", "$C_1$-$C_6$ alkyl aryl", "$C_1$-$C_6$ alkyl heteroaryl", "$C_3$-$C_8$-cycloalkyl," or "heterocycloalkyl," and where R and R', together with the nitrogen atom to which they are attached, can optionally form a 3-8-membered heterocycloalkyl ring.

The term "ammonium $C_1$-$C_6$ alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —OSO$_2$—R wherein R is selected from "$C_1$-$C_6$ alkyl," "$C_1$-$C_6$ alkyl" substituted with halogens, e.g., an —OSO$_2$—CF$_3$ group, "$C_2$-$C_6$ alkenyl," "$C_2$-$C_6$ $C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfamate" refers to a group —OSO$_2$—NRR' wherein R and R' are independently selected from H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl" and the like.

The term "sulfonyloxy $C_1$-$C_6$ alkyl" refers to alkyl groups having a sulfonyloxy substituent, including 2-(methylsulfonyloxy)ethyl and the like.

The term "sulfonyl" refers to group "—SO$_2$—R" wherein R is selected from "aryl," "heteroaryl," "$C_1$-$C_6$ alkyl," "$C_1$-$C_6$ alkyl" substituted with halogens, e.g., an —SO$_2$—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonyl $C_1$-$C_6$ alkyl" refers to alkyl groups having a sulfonyl substituent, including 2-(methylsulfonyl)ethyl and the like.

The term "sulfinyl" refers to a group "—S(O)—R" wherein R is selected from "$C_1$-$C_6$ alkyl," "$C_1$-$C_6$ alkyl" substituted with halogens, e.g., a —SO—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfinyl $C_1$-$C_6$ alkyl" refers to alkyl groups having a sulfinyl substituent, including 2-(methylsulfinyl)ethyl and the like.

The term "sulfanyl" refers to groups —S—R where R includes H, halogens, e.g. a —SF$_5$ group, optionally substituted "$C_1$-$C_6$ alkyl," in particular "$C_1$-$C_6$ alkyl" substituted with halogens, e.g., a —S—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "alkynylheteroaryl," "$C_3$-$C_8$-cycloalkyl $C_1$-$C_6$ alkyl," or "heterocycloalkyl $C_1$-$C_6$ alkyl".

The term "sulfanyl $C_1$-$C_6$ alkyl" refers to $C_1$-$C_5$-alkyl groups having a sulfanyl substituent, including 2-(ethylsulfanyl)ethyl and the like.

The term "sulfonylamino" refers to a group —NRSO$_2$—R' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonylamino $C_1$-$C_6$ alkyl" refers to alkyl groups having a sulfonylamino substituent, including 2-(ethylsulfonylamino)ethyl and the like.

The term "aminosulfonyl" refers to a group —SO$_2$—NRR' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl $C_1$-$C_6$ alkyl" refers to $C_1$-$C_6$ alkyl groups having an aminosulfonyl substituent, including 2-(cyclohexylaminosulfonyl)ethyl and the like.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl $C_3$-$C_8$-cycloalkyl," "$C_1$-$C_6$ alkyl heterocycloalkyl," "acyl", "amino," "amide", "aminosulfonyl," "ammonium," "acyl amino," "aminocarbonyl," "aryl," "heteroaryl," "sulfinyl," "sulfonyl," "sulphonamide", "alkoxy," "alkoxy carbonyl," "carbamate," "sulfanyl," "halogen," trihalomethyl, cyano, hydroxy, mercapto, nitro, and the like.

In a particular embodiment, the term optionally substituted "$C_1$-$C_6$ alkyl" includes optionally substituted halogenated "$C_1$-$C_6$ alkyl" such as fluorinated "$C_1$-$C_6$ alkyl" (e.g. —$CF_3$, —$CF_3CH_2$ or —$CF_3CF_2$).

The term "pharmaceutically acceptable salts or complexes" refers to salts or complexes of the compounds according to the invention. Examples of such salts include, but are not restricted, to base addition salts formed by reaction of aminopyrazine derivatives of the invention with organic or inorganic bases such as hydroxide, carbonate or bicarbonate of a metal cation such as those selected in the group consisting of alkali metals (sodium, potassium or lithium), alkaline earth metals (e.g. calcium or magnesium).

Are also comprised salts which are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid. "Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compounds according to the invention and presenting anti-malarial activity that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g. by oxidation, reduction, hydrolysis or the like, each of which is carried out enzymatically.

These compounds can be produced from compounds of the present invention according to well-known methods.

The term "indirectly" also encompasses metabolites of compounds according to the invention.

The term "metabolite" refers to all molecules derived from any of the compounds according to the present invention in a cell or organism, preferably mammal.

In the context of the present invention are encompassed pharmaceutically acceptable salts, complexes, hydrates, solvates, or polymorphs, tautomers, geometrical isomers, optically active forms and pharmaceutically active derivatives of compounds of the invention. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. Many organic compounds exist in optically active forms having the ability to rotate the plane of plane-polarized light. In describing an optically active compound, the prefixes D and L or R and S are used to denote the absolute configuration of the molecule about its chiral center(s).

The term "malaria" includes disease and conditions related to an infection by *Plasmodium*.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "effective amount" includes "prophylaxis-effective amount" as well as "treatment-effective amount".

The term "prophylaxis-effective amount" refers to a concentration of compound of this invention that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites.

The term "prophylaxis" includes causal prophylaxis, i.e. antimalarial activity comprising preventing the pre-erythrocytic development of the parasite, suppressive prophylaxis, i.e. antimalarial activity comprising suppressing the development of the blood stage infection and terminal prophylaxis, i.e. antimalarial activity comprising suppressing the development of intra-hepatic stage infection. This term includes primary prophylaxis (i.e. preventing initial infection) where the antimalarial compound is administered before, during and/or after the exposure period to malarial parasites and terminal prophylaxis (i.e. to prevent relapses or delayed onset of clinical symptoms of malaria) when the antimalarial compound is administered towards the end of and/or slightly after the exposure period to malarial parasites but before the clinical symptoms. Typically, against *P. falciparum* infections, suppressive phophylaxis is used whereas against *P. vivax* or a combination of *P. falciparum* and *P. vivax*, terminal prophylaxis is used.

Likewise, the term "treatment-effective amount" refers to a concentration of compound that is effective in treating malaria infection, e.g. leads to a reduction in parasite numbers in blood following microscopic examination when administered after infection has occurred.

The term "subject" as used herein refers to mammals. For examples, mammals contemplated by the present invention include humans and the like.

Compounds

According to one embodiment, is a provided aminopyrazine derivative according to Formula (I):

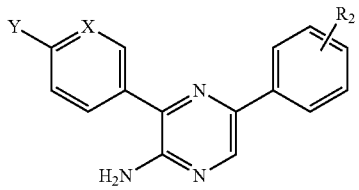

(I)

wherein X is $CR^1$ or N; Y is selected from $CF_3$, —C(O)—$NR^3R^4$; O—$R^6$; $SO_2$—$R^6$; $R^1$ is selected from H and halogen such as F; $R^2$ is selected from $SO_2$—$R^5$ and —C(O)—$R^{10}$; $R^3$ and $R^4$ are independently selected from H and optionally substituted $C_1$-$C_6$ alkyl such as optionally substituted methyl (e.g. methyl); $R^5$ is selected from —$NR^7R^8$ and $R^9$; $R^6$ is optionally substituted $C_1$-$C_6$ alkyl such as optionally substituted methyl (e.g. methyl); $R^7$ and $R^8$ are independently selected from H and optionally substituted $C_1$-$C_6$ alkyl such as optionally substituted methyl (e.g. methyl); $R^9$ is optionally substituted $C_1$-$C_6$ alkyl such as $C_1$-$C_6$ alkyl optionally substituted by $C_1$-$C_6$ alkyl or by $C_3$-$C_8$ cycloalkyl, for example optionally substituted cyclopropyl, optionally substituted methyl (e.g. methyl, methyl cyclopropyl), optionally substituted ethyl (e.g. ethyl), optionally substituted propyl (e.g. isopropyl) or optionally substituted $C_3$-$C_8$ cycloalkyl; $R^{10}$ is —$NR^{11}R^{12}$; $R^{11}$ and $R^{12}$ are independently selected from H and optionally substituted $C_1$-$C_6$ alkyl or $NR^{11}R^{12}$ form together an optionally substituted heterocycloalkyl such as optionally substituted piperazine (e.g. piperazine optionally substituted with $C_1$-$C_6$ alkyl like piperazin-1-yl, 4-methyl piperazin-1-yl or 4-t-butyl piperazin-1-yl), optionally substituted morpholinyl (e.g. morpholino), optionally substituted diazepan (e.g. diazepan optionally substituted with $C_1$-$C_6$ alkyl like 1,4 diazepan or 4-methyl 1,4 diazepan), optionally substituted pyrrolidin (e.g. pyrrolidin optionally substituted by amino or hydroxy like 3-hydroxy pyrrolidin-1-yl or 3-amino pyrrolidin-1-yl), optionally substituted piperidine (e.g. piperidine optionally substituted by hydroxy or amino like 4-hydroxy piperidin-1-yl, 4-amino piperidin-1-yl); as well as pharmaceutically acceptable salts, complexes, hydrates, solvates, or polymorphs, tautomers, geometrical isomers, optically active forms and pharmaceutically active derivative thereof.

In a particular embodiment, the invention provides an aminopyrazine derivative according to the invention wherein X is N.

In a particular embodiment, the invention provides an aminopyrazine derivative according to the invention wherein X is N and Y is selected from $CF_3$ and O—$R^6$.

In another particular embodiment, the invention provides an aminopyrazine derivative according to the invention wherein X is $CR^1$.

In another particular embodiment, the invention provides an aminopyrazine derivative according to the invention wherein $R^1$ is H.

In another particular embodiment, the invention provides an aminopyrazine derivative according to the invention wherein $R^1$ is halogen, in particular fluoro.

In another particular embodiment, the invention provides an aminopyrazine derivative according to the invention wherein Y is $CF_3$.

In another particular embodiment, the invention provides an aminopyrazine derivative according to the invention wherein Y is —C(O)—$NHR^3$.

In another particular embodiment, the invention provides an aminopyrazine derivative according to the invention wherein $R^3$ is H.

In another particular embodiment, the invention provides an aminopyrazine derivative according to the invention wherein $R^4$ is optionally substituted $C_1$-$C_6$ alkyl such as optionally substituted methyl (e.g. methyl).

In another particular embodiment, the invention provides an aminopyrazine derivative according to the invention wherein Y is $SO_2$—$R^6$.

In another particular embodiment, the invention provides an aminopyrazine derivative according to the invention wherein $R^6$ is optionally substituted methyl (e.g. methyl).

In a further particular embodiment, the invention provides an aminopyrazine derivative according to the invention wherein X is $CR^1$, $R^1$ is H and Y is selected from C(O)—$NHR^3$ and $SO_2$—$R^6$.

In a further particular embodiment, the invention provides an aminopyrazine derivative according to the invention wherein X is $CR^1$, $R^1$ is H and Y is $CF_3$.

In another particular embodiment, the invention provides an aminopyrazine derivative according to the invention wherein $R^2$ is in para position of the phenyl ring.

In another particular embodiment, the invention provides an aminopyrazine derivative according to the invention wherein $R^2$ is $SO_2$—$R^5$.

In a further particular embodiment, the invention provides an aminopyrazine derivative according to the invention wherein $R^5$ is —$NR^7R^8$.

In a further particular embodiment, the invention provides an aminopyrazine derivative according to the invention wherein $R^7$ is H.

In a further particular embodiment, the invention provides an aminopyrazine derivative according to the invention wherein $R^8$ is H.

In a further particular embodiment, the invention provides an aminopyrazine derivative according to the invention wherein $R^8$ is optionally substituted $C_1$-$C_6$ alkyl such as optionally substituted methyl (e.g. methyl).

In another further particular embodiment, the invention provides an aminopyrazine derivative according to the invention wherein $R^5$ is $R^9$.

In another further particular embodiment, the invention provides an aminopyrazine derivative according to the invention wherein $R^9$ is optionally substituted $C_1$-$C_6$ alkyl.

In another further particular embodiment, the invention provides an aminopyrazine derivative according to the invention wherein $R^9$ is $C_1$-$C_6$ alkyl optionally substituted by $C_1$-$C_6$ alkyl or by $C_3$-$C_8$ cycloalkyl.

In another further particular embodiment, the invention provides an aminopyrazine derivative according to the invention wherein $R^9$ is optionally substituted $C_3$-$C_8$ cycloalkyl.

In another further particular embodiment, the invention provides an aminopyrazine derivative according to the invention wherein $R^9$ is optionally substituted methyl (e.g. methyl), optionally substituted ethyl (e.g. ethyl) and optionally substituted propyl (e.g. isopropyl).

In another particular embodiment, the invention provides an aminopyrazine derivative according to the invention wherein $R^2$ is —C(O)—$R^{10}$.

In another particular embodiment, the invention provides an aminopyrazine derivative according to the invention wherein $R^{11}$ and $R^{12}$ are independently selected from H and optionally substituted $C_1$-$C_6$ alkyl.

In another particular embodiment, the invention provides an aminopyrazine derivative according to the invention wherein $NR^{11}R^{12}$ form together an optionally substituted heterocycloalkyl such as optionally substituted piperazine (e.g. piperazine optionally substituted with $C_1$-$C_6$ alkyl like piperazin-1-yl, 4-methyl piperazin-1-yl or 4-t-butyl piperazin-1-yl), optionally substituted morpholinyl (e.g. morpholino), optionally substituted diazepan (e.g. diazepan optionally substituted with $C_1$-$C_6$ alkyl like 1,4 diazepan or 4-methyl 1,4 diazepan), optionally substituted pyrrolidin (e.g. pyrrolidin optionally substituted by amino or hydroxy like 3-hydroxy pyrrolidin-1-yl, 3-amino pyrrolidin-1-yl), optionally substituted piperidine (e.g. piperidine optionally substituted by hydroxy or amino like 4-hydroxy piperidin-1-yl, 4-amino piperidin-1-yl).

In another particular embodiment, the invention provides an aminopyrazine derivative according to the invention wherein $R^2$ is —C(O)—$NR^{11}R^{12}$ and $NR^{11}R^{12}$ form together an optionally substituted pyrrolidine.

In a particular embodiment is provided an aminopyrazine derivative selected from the following group:
3-(6-methoxypyridin-3-yl)-5-(4-(methylsulfonyl)phenyl)pyrazin-2-amine;
5-(4-(methylsulfonyl)phenyl)-3-(4-(trifluoromethyl)phenyl)pyrazin-2-amine
5-(4-(methylsulfonyl)phenyl)-3-(6-(trifluoromethyl)pyridin-3-yl)pyrazin-2-amine;
4-(5-amino-6-(4-(trifluoromethyl)phenyl)pyrazin-2-yl)benzamide;
4-(5-amino-6-(6-(trifluoromethyl)pyridin-3-yl)pyrazin-2-yl)benzamide;
(4-(5-amino-6-(4-(trifluoromethyl)phenyl)pyrazin-2-yl)phenyl)(4-methylpiperazin-1-yl) methanone;
(4-(5-amino-6-(6-(trifluoromethyl)pyridin-3-yl)pyrazin-2-yl)phenyl)(4-methylpiperazin-1-yl)methanone;
(4-(5-amino-6-(4-(trifluoromethyl)phenyl)pyrazin-2-yl)phenyl)(piperazin-1-yl)methanone;
(4-(5-amino-6-(6-(trifluoromethyl)pyridin-3-yl)pyrazin-2-yl)phenyl)(piperazin-1-yl) methanone;
(4-(5-amino-6-(6-(trifluoromethyl)pyridin-3-yl)pyrazin-2-yl)phenyl)(morpholino) methanone;
(4-(5-amino-6-(4-(trifluoromethyl)phenyl)pyrazin-2-yl)phenyl)(morpholino)methanone;
(4-(5-amino-6-(6-(trifluoromethyl)pyridin-3-yl)pyrazin-2-yl)phenyl)(4-methyl-1,4-diazepan-1-yl)methanone;
4-(5-amino-6-(3-fluoro-4-(trifluoromethyl)phenyl)pyrazin-2-yl)benzamide;
4-(5-amino-6-(4-(methylsulfonyl)phenyl)pyrazin-2-yl)benzamide;
4,4'-(3-aminopyrazine-2,6-diyl)dibenzamide;
4-(3-amino-6-(4-carbamoylphenyl)pyrazin-2-yl)-N-methylbenzamide;
4-(5-amino-6-(6-(trifluoromethyl)pyridin-3-yl)pyrazin-2-yl)-N-methylbenzene sulfonamide;
5-(4-(ethylsulfonyl)phenyl)-3-(6-(trifluoromethyl)pyridin-3-yl)pyrazin-2-amine;
5-(4-(isopropylsulfonyl)phenyl)-3-(6-(trifluoromethyl)pyridin-3-yl)pyrazin-2-amine;
(4-(5-amino-6-(4-(trifluoromethyl)phenyl)pyrazin-2-yl)phenyl)(4-(tert-butyl)piperazin-1-yl)methanone;
(4-(5-amino-6-(4-(trifluoromethyl)phenyl)pyrazin-2-yl)phenyl)(3-hydroxypyrrolidin-1-yl)methanone;
(4-(5-amino-6-(6-(trifluoromethyl)pyridin-3-yl)pyrazin-2-yl)phenyl)(4-hydroxy piperidin-1-yl)methanone;
(4-(5-amino-6-(4-(trifluoromethyl)phenyl)pyrazin-2-yl)phenyl)(4-hydroxypiperidin-1-yl)methanone;
(4-(5-amino-6-(6-(trifluoromethyl)pyridin-3-yl)pyrazin-2-yl)phenyl)(4-(tert-butyl) piperazin-1-yl)methanone;
(4-(5-amino-6-(4-(trifluoromethyl)phenyl)pyrazin-2-yl)phenyl)(4-methyl-1,4-diazepan-1-yl)methanone;
(4-(5-amino-6-(6-(trifluoromethyl)pyridin-3-yl)pyrazin-2-yl)phenyl)(1,4-diazepan-1-yl)methanone;
(4-(5-amino-6-(4-(trifluoromethyl)phenyl)pyrazin-2-yl)phenyl)(1,4-diazepan-1-yl) methanone;
(4-(5-amino-6-(6-(trifluoromethyl)pyridin-3-yl)pyrazin-2-yl)phenyl)(3-aminopyrrolidin-1-yl)methanone;
(4-(5-amino-6-(4-(trifluoromethyl)phenyl)pyrazin-2-yl)phenyl)(3-aminopyrrolidin-1-yl)methanone;
(4-(5-amino-6-(6-(trifluoromethyl)pyridin-3-yl)pyrazin-2-yl)phenyl)(3-hydroxy pyrrolidin-1-yl)methanone;
(4-(5-amino-6-(6-(trifluoromethyl)pyridin-3-yl)pyrazin-2-yl)phenyl)(4-amino cyclohexyl)methanone;
(4-(5-amino-6-(4-(trifluoromethyl)phenyl)pyrazin-2-yl)phenyl)(4-aminocyclohexyl)methanone;
5-(4-(cyclopropylmethylsulfonyl)phenyl)-3-(6-(trifluoromethyl)pyridin-3-yl)pyrazin-2-amine; and
5-(4-(cyclopropylsulfonyl)phenyl)-3-(6-(trifluoromethyl)pyridin-3-yl)pyrazin-2-amine;
as well as pharmaceutically acceptable salts, complexes, hydrates, solvates, or polymorphs, tautomers, geometrical isomers, optically active forms and pharmaceutically active derivative thereof.

In another particular embodiment is provided the aminopyrazine derivative (4-(5-amino-6-(4-(trifluoromethyl)phenyl)pyrazin-2-yl)phenyl)(3-hydroxypyrrolidin-1-yl)methanone, in particular its (S)-(4-(5-amino-6-(4-(trifluoromethyl)phenyl)pyrazin-2-yl)phenyl) (3-hydroxypyrrolidin-1-yl)methanone enantiomer.

In another particular embodiment is provided the aminopyrazine derivative (4-(5-amino-6-(4-(trifluoromethyl)phenyl)pyrazin-2-yl)phenyl)(3-hydroxypyrrolidin-1-yl) methanone, in particular its (R)-(4-(5-amino-6-(4-(trifluoromethyl)phenyl)pyrazin-2-yl)phenyl) (3-hydroxypyrrolidin-1-yl)methanone enantiomer.

The aminopyrazine derivatives used in the manufacture of a medicament for the prevention or treatment of malaria, are capable of killing and/or inhibiting malaria parasite replication.

Compositions

The invention provides pharmaceutical compositions useful for the prophylaxis or treatment of malaria. The invention further provides methods for treating a mammalian patient, and most preferably a human patient, who is suffering from malaria.

In another particular embodiment, is provided a pharmaceutical formulation containing at least one derivative according the invention and a pharmaceutically acceptable carrier, diluent or excipient thereof.

In another particular embodiment, is provided a pharmaceutical formulation comprising an aminopyrazine according to Formula (I) and an antimalarial agent as defined in the detailed description.

Pharmaceutical compositions of the invention can contain one or more compound(s) of the invention in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended dosage range to be employed. Compositions according to the invention are preferably oral.

Compositions of this invention may be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's Pharmaceutical Sciences*, 21$^{st}$ Edition, 2005, University of the Sciences in Philadelphia, Lippincott Williams & Wilkins, which is incorporated herein by reference. Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides.

Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, sublingually, transdermally, vaginally, rectally, transmucosally, topically, via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion. In a preferred embodiment, aminopyrazine derivatives according to the invention are administered orally.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to the invention, the aminopyrazine derivatives of the invention and pharmaceutical formulations thereof can be administered alone or in combination with a co-agent useful in the treatment of malaria, such as substances useful in the treatment and/or prevention of malaria e.g. for example a co-agent including, but not limited to, artemisinin or an artemisinin derivative (such as artemether or dihydroartemisinin), chloroquine, mefloquine, quinine, atovaquone/proguanil, doxycycline, hydroxychloroquine, halofantrine, pyronaridine, lumefantrine, pyrimethamine-sulfadoxine and piperaquine.

Further co-agent useful in the context of the invention are selected from quinacrine, chloroquine, primaquine, doxycycline, atovaquone, proguanil hydrochloride, ferroquine, tafenoquine, arterolane, Spiro[3H-indole-3,1'-[1H]pyrido[3,4-b]indol]-2(1H)-one (CAS Registry Number: 1193314-23-6), 5,7'-dichloro-6'-fluoro-2',3',4',9'-tetrahydro-3'-methyl-(1'R, 3'S)—], Sulfur, [4-[[2-(1,1-difluoroethyl)-5-methyl[1,2,4]triazolo[1,5-a]pyrimidin-7-yl]amino]phenyl]pentafluoro-] (CAS Registry Number: 1282041-94-4), Morpholine, and 4-[2-(4-cis-dispiro[cyclohexane-1,3'-[1,2,4]trioxolane-5', 2"-tricyclo[3.3.1.13,7]decan]-4-ylphenoxy)ethyl]-] (CAS Registry Number: 1029939-86-3).

The invention encompasses the administration of an aminopyrazine derivative according to the invention or of a pharmaceutical formulation thereof, wherein the aminopyrazine derivatives or the pharmaceutical formulation thereof is administered to an individual prior to, simultaneously or sequentially with other therapeutic regimens or co-agents useful in the treatment of malaria (e.g. multiple drug regimens), in an effective amount. Aminopyrazine derivatives or the pharmaceutical formulations thereof that are administered simultaneously with said co-agents can be administered in the same or different composition(s) and by the same or different route(s) of administration.

Patients

In an embodiment, patients according to the invention are patients suffering from malaria.

In another embodiment, patients according to the invention are patients with a high risk of being infected by *Plasmodium*.

In another embodiment, patients according to the invention are patients with a high risk of being infected by *Plasmodium falciparum*.

In another embodiment, patients according to the invention are patients with a high risk of being infected by *Plasmodium vivax*.

Use According to the Invention

In one embodiment, the invention provides a use of an aminopyrazine derivative according to Formula (I):

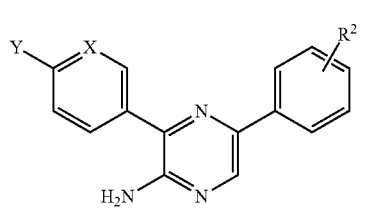

(I)

wherein X is $CR^1$ or N; Y is selected from $CF_3$, —C(O)—$NR^3R^4$; O—$R^6$; $SO_2$—$R^6$; $R^1$ is selected from H and halogen; $R^2$ is selected from $SO_2$—$R^5$ and —C(O)—$R^{10}$; $R^3$ and $R^4$ are independently selected from H and optionally substituted $C_1$-$C_6$ alkyl; $R^5$ is selected from —$NR^7R^8$ and $R^9$; $R^6$ is optionally substituted $C_1$-$C_6$ alkyl; $R^7$ and $R^8$ are independently selected from H and optionally substituted $C_1$-$C_6$ alkyl; $R^9$ is optionally substituted $C_1$-$C_6$ alkyl and optionally substituted $C_3$-$C_5$ cycloalkyl; $R^{10}$ is —$NR^{11}R^{12}$; $R^{11}$ and $R^{12}$ are independently selected from H and optionally substituted $C_1$-$C_6$ alkyl or $NR^{11}R^{12}$ form together an optionally substituted heterocycloalkyl; as well as pharmaceutically acceptable salts, complexes, hydrates, solvates, or polymorphs, tautomers, geometrical isomers, optically active forms and pharmaceutically active derivative thereof for the preparation of a pharmaceutical composition for the treatment or prophylaxis of malaria.

In another embodiment, the invention provides a method for preventing or treating malaria in a patient. The method comprises administering an effective amount of an aminopyrazine derivative according to the invention, or a pharmaceutically acceptable salt or a pharmaceutically active derivative thereof or a pharmaceutical formulation thereof in a patient in need thereof.

In another embodiment, the invention provides an aminopyrazine derivative according to the invention as well as pharmaceutically acceptable salts or a pharmaceutically active derivative thereof or a pharmaceutical formulation thereof, for use in the treatment or prophylaxis of malaria.

In another embodiment, the invention provides a use of an aminopyrazine derivative or a method according to the invention wherein the aminopyrazine derivative is to be administered in combination with a co-agent useful in the treatment of malaria.

In another embodiment, the invention provides a pharmaceutical composition comprising an aminopyrazine derivative according to the invention in combination with a co-agent useful in the treatment of malaria.

In another embodiment, the invention provides a process for the preparation of an aminopyrazine derivative according to the invention comprising the step of reacting a derivative according to Formula (v) with a boronic acid of Formula (vi) under Suzuki reaction conditions (Miyaura et al., 1995, *Chem. Rev.*, 95 (7), pp 2457-2483) to lead to a compound of Formula (I):

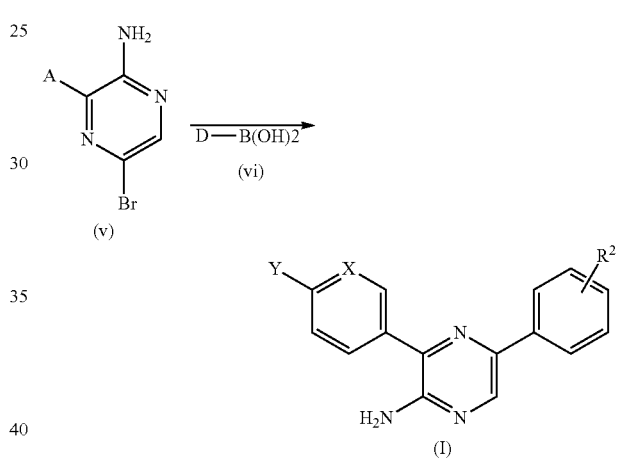

wherein A is

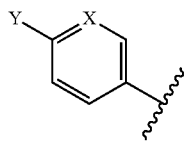

and D is:

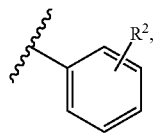

X, Y, $R^1$ and $R^2$ are as described herein.

In another embodiment, the invention provides an intermediate of Formula (v) wherein A is as defined herein.

In another further embodiment, the invention provides an intermediate of Formula (v), wherein the intermediate is 5-bromo-3-(6-methoxypyridin-3-yl)pyrazin-2-amine.

In another embodiment, the invention provides a process for the preparation of an aminopyrazine derivative according to the invention comprising the step of reacting a derivative according to Formula (viii) with a boronic acid of Formula (iv) under Suzuki reaction conditions (Miyaura et al., 1995, supra) to lead to a compound of Formula (I):

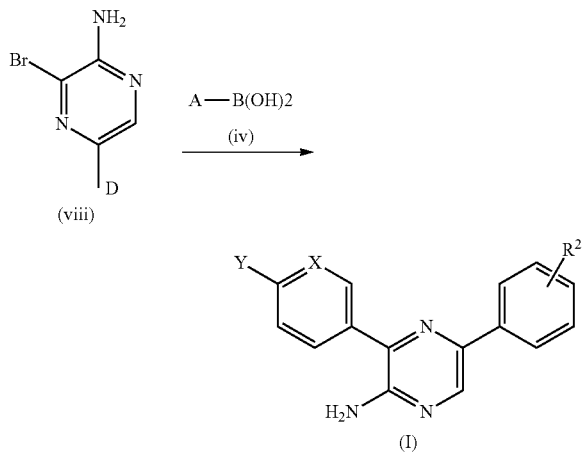

A, D, X, Y and R¹ as described herein.

In another embodiment, the invention provides an intermediate of Formula (viii) wherein D is as defined herein.

In another further embodiment, the invention provides an intermediate of Formula (viii), wherein the intermediate is 3-bromo-5-(4-(methylsulfonyl)phenyl)pyrazin-2-amine.

In another further embodiment, the invention provides an intermediate of Formula (viii), wherein the intermediate is (4-(5-amino-6-bromopyrazin-2-yl)phenyl)(3-hydroxypyrrolidin-1-yl)methanone.

In another embodiment, the invention provides a process for the preparation of an aminopyrazine derivative according to the invention comprising the step of reacting a derivative according to Formula (xix) in TFA to lead to a compound of Formula (V), i.e. a compound of Formula (I) wherein R² is in para of the phenyl ring and is R² is —C(O)—R¹⁰, NR¹¹R¹² form together a piperazine:

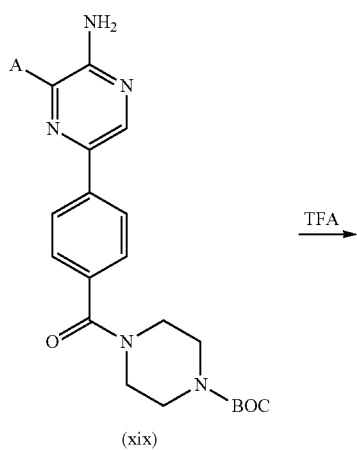

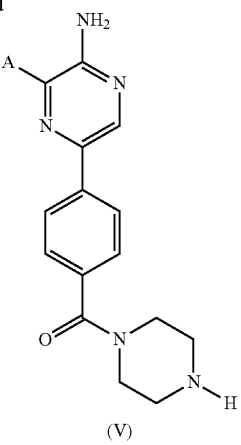

wherein A, X, Y and R¹ as described herein.

In another embodiment, the invention provides an intermediate of Formula (xix) wherein A is as defined herein.

In another embodiment, the invention provides an intermediate of Formula (xix) selected from the following group:
tert-butyl 4-(4-(5-amino-6-(4-(trifluoromethyl)phenyl) pyrazin-2-yl)benzoyl)piperazine-1-carboxylate and tert-butyl 4-(4-(5-amino-6-(6-(trifluoromethyl)pyridin-3-yl) pyrazin-2-yl)benzoyl) piperazine-1-carboxylate.

In another embodiment, the invention provides a process for the preparation of an intermediate of formula (xv) comprising a step of reacting an intermediate of formula (xiv) in presence of N-methyl piperazine (e.g. as described in Scheme 3).

In another embodiment, the invention provides an intermediate of Formula (xiv).

In another embodiment, the invention provides an intermediate of Formula (xv).

In another embodiment, the invention provides a process for the preparation of an intermediate of Formula (xviii) comprising a step of reacting an intermediate of formula (xvii) in presence of N-bromosuccinimide (e.g. as described in Scheme 4).

In another embodiment, the invention provides an intermediate of Formula (xviii).

In another embodiment, the invention provides an intermediate of Formula (xvii).

In another embodiment, the invention provides a process for the preparation of an intermediate of Formula (xvii) comprising a step of reacting an intermediate of formula (xiv) in presence of N-Boc piperazine (e.g. as described in Scheme 4).

In another embodiment, the invention provides a process for the preparation of an intermediate of Formula (xxiv) comprising a step of reacting an intermediate of formula (xxiii) in presence of 1-methyl homo piperazine (e.g. as described in Scheme 5).

In another embodiment, the invention provides an intermediate of Formula (xxiv).

In another embodiment, the invention provides an intermediate of Formula (xxiii).

In another embodiment, the invention provides a process for the preparation of an intermediate of Formula (xxiii) comprising a step of reacting an intermediate of formula (xxii) in presence of lithium oxide (e.g. as described in Scheme 5).

In another embodiment, the invention provides an intermediate of Formula (xxii).

In another embodiment, the invention provides a process for the preparation of an intermediate of Formula (xxii) comprising a step of reacting an intermediate of formula (xiv) in presence of N-bromosuccinimide (e.g. as described in Scheme 5).

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

In the following the present invention shall be illustrated by means of some examples, which are not to be viewed as limiting the scope of the invention.

EXAMPLES

The following abbreviations refer respectively to the definitions below:

g (gram), h (hour), mmol (millimole), RT (room temperature), DCM (dichloromethane), DMF (N,N-Dimethylformamide), DMSO (Dimethyl Sulfoxide), EDCI (1-Ethyl-3-(3-dimethylaminopropyl)carbodiimide), HOBt (N-Hydroxybenzotriazole), LC (Liquid chromatography), MS (Mass Spectrometry), MHz (Megaherz), NBS (N-bromosuccinimide), NMR (Nuclear magnetic resonance), TFA (Trifluoroacetic acid), THF (Tetrahydrofuran), TLC (Thin layer chromatography), UV (Ultraviolet).

The compounds of invention have been named according to the IUPAC standards used in the program ChemDraw Ultra (Version 12.0).

The MS, NMR and IR data provided in the examples described below are obtained as followed: The MS, NMR and IR data provided in the examples described below are obtained as followed: Mass spectra: Waters ZQ API MS system+Binary HPLC system with Ultra Violet Diode Array Detector; $H^1$ NMR and $C^{13}$ NMR spectra were recorded on either a Varian Mercury-300 (300 MHz) or Bruker Advance III 400 (400 MHz) with Ultra Shield™ 400 Plus magnet spectrometer in $CDCl_3$ solution unless otherwise indicated and chemical shifts are reported as δ (ppm) down field from the solvent signal as internal standard for $H^1$ and $C^{13}$ NMR. Infrared spectra were recorded on a PerkinElmer Paragon 1000 FT-IR spectrometer using DCM as solvent. TLC was performed on Merck 60$F_{254}$ silica plates and visualised by UV light. The compounds were purified by wet flash chromatography using Merck Kieselgel 60 (particle size 70-230 mesh) silica under gravity. The compounds were purified by HPLC using a Hypersil BDS C18 column, 2 μL injection volume, flow 0.7 mL/min; gradient: 10-70% B in 20 min, 70-100% B in 10 min, (hold 5 min), 100-10% in 3 min (hold 7 min) (Mobile phase A: 0.1% TFA in $H_2O$ and Mobile phase B: Methanol) with PDA-maximum chromatogram (210-400 nm).

Example 1

Synthesis of Compounds According to the Invention

The aminopyrazine derivatives can be prepared from readily available starting materials using methods and procedures known from the skilled person. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

A general synthetic approach for obtaining compounds of Formula (I) is depicted in Scheme 1 below. Aminopyrazine derivatives according to Formula (I), whereby the substituents are as above defined, may be prepared in four steps, from custom made or commercially available aminopyrazines according to formula (i), 5-bromo-pyrazine-2-amine according to formula (ii), 5-bromo-3-iodopyrazine-2-amine of formula (iii), or boronic acids of formulae (iv) or (vi) and substituted 5-bromopyrazine-2-amine derivatives according to formula (v), according to formula (iv), following the synthetic pathway as outlined in Scheme 1 below.

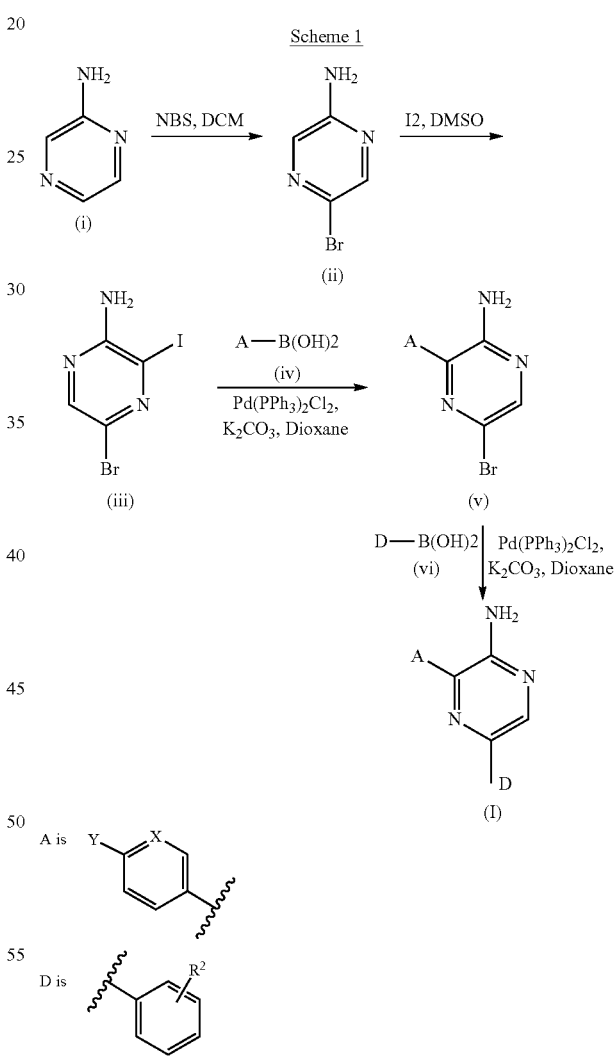

To a solution of 2-aminopyrazine (i) (2 g, 21.02 mmol) in dry DCM (10 ml) was added NBS (3.78 g, 21.23 mmol) portion-wise under cold condition and the resulting mixture was allowed to stir at RT for 6 h. 5 ml of water was added and the layers were separated. Aqueous layer was extracted with DCM (10 ml×2). Combined organic layers were washed with Brine solution (5 ml), dried over anhydrous $Na_2SO_4$ and concentrated under vacuum. Crude material was purified by column chromatography over silica gel 230-400 mesh by using 18% of ethyl acetate in petroleum ether as an eluent to afford compound (ii) (1.98 g, 54.42%) as white solid.

To a solution of compound (ii) (1.98 g, 11.46 mmol) in DMSO (20 ml) was added iodine crystals (3.49 g, 13.75 mmol) at RT and the resulting mixture was heated to 100° C. for 4 h and then stirred at RT for 12 h. Water (20 ml) was then added and the reaction mixture was extracted with ethyl acetate (60 ml×4). Combined organic layers were washed with water (10 ml×3), saturated sol. of sodium metabisulphite (5 ml× till Iodine color disappears), Brine solution (10 ml), dried over anhydrous $Na_2SO_4$ and concentrated under vacuum. The crude material was purified by column chromatography over silica gel 230-400 mesh by using ethyl acetate in petroleum ether as an eluent to yield compound (iii) (260 mg, 7.56%) as white solid.

To the solution of compound (iii) (355 mg, 1.18 mmol) in 1,4-dioxane (5 ml) was added a boronic acid of formula (iv) such as 6-methoxypyridin-3-yl boronic acid (CombiBlocks 190 mg, 1.24 mmol) at RT and the reaction mixture was purged with $N_2$ gas for 30 minutes. Bis(triphenylphosphine) palladium(II)chloride (58 mg, 0.08 mmol) and 1 M aqueous solution of potassium carbonate (1.42 ml, pre-purged with $N_2$ gas) were added to the reaction mixture. The solution was heated to reflux for 16 h and then cooled to RT, added Brine solution (5 ml) and extracted with ethyl acetate (10 ml×4). Combined organic layers were dried over anhydrous $Na_2SO_4$ and concentrated. Crude material was purified by column chromatography over silica gel 230-400 mesh by using 1-2% MeOH in DCM as an eluent to yield compound (v) (150 mg, 45.18%) as solid. To the solution of compound (v) (240 mg, 0.85 mmol) in 1,4-dioxane (3 ml) was added a boronic acid of formula (vi) such as 4-methylsulphonyphenylboronicacid (CombiBlocks) (187 mg, 0.93 mmol) at RT in a seal tube and the solution was purged with $N_2$ gas for 30 minutes. Bis (triphenylphosphine)palladium(II)chloride (41 mg, 0.059 mmol) and 1 M aqueous solution of potassium carbonate (1.02 ml, pre-purged with $N_2$ gas) were added to the reaction mixture. The resulting solution was heated to 110° C. for 16 h, cooled to RT, added Brine solution (3 ml) and extracted with Ethyl acetate (7 ml×4). Combined organic layers were dried over anhydrous $Na_2SO_4$ and concentrated under vacuum. Crude material was purified by column chromatography over silica gel 230-400 mesh by using 2-3% of MeOH in DCM as an eluent to yield to a compound of Formula (I) such as compound (1) (63.25 mg, 24.23%) as solid.

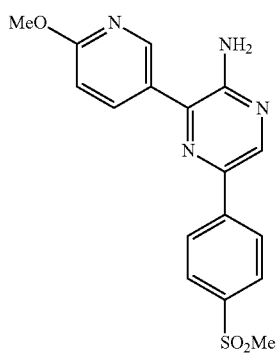

(1)

3-(6-methoxypyridin-3-yl)-5-(4-(methylsulfonyl)phenyl) pyrazin-2-amine; MS m/z [M+H]+: 357.2; 400 MHz, DMSO-d6: δ 8.70 (s, 1H), 8.60 (s, 1H), 8.26 (d, J=8.20 Hz, 2H), 8.11 (d, J=7.52 Hz, 1H), 7.97 (d, J=8.12 Hz, 2H), 6.98 (d, J=8.56 Hz, 1H), 6.71 (s, 1H), 3.94 (s, 3H), 3.24 (s, 3H).

Alternatively, compounds of Formula (I) wherein $R^2$ is $SO_2$—$R^5$ and —C(O)—$R^{10}$; $R^3$ and $R^4$ are independently selected from H and optionally substituted $C_1$-$C_6$ alkyl; $R^5$ is selected from —$NR^7R^8$ and $R^9$; $R^6$ is optionally substituted $C_1$-$C_6$ alkyl; $R^7$ and $R^8$ are independently selected from H and optionally substituted $C_1$-$C_6$ alkyl; $R^9$ is optionally substituted $C_1$-$C_6$ alkyl; $R^{10}$ is —$NR^{11}R^{12}$; $R^{11}$ and $R^{12}$ are independently selected from H and optionally substituted $C_1$-$C_6$ alkyl or $NR^{11}R^{12}$ form together an optionally substituted heterocycloalkyl being an optionally substituted morpholino group can be obtained as depicted in Scheme 2 below:

Scheme 2

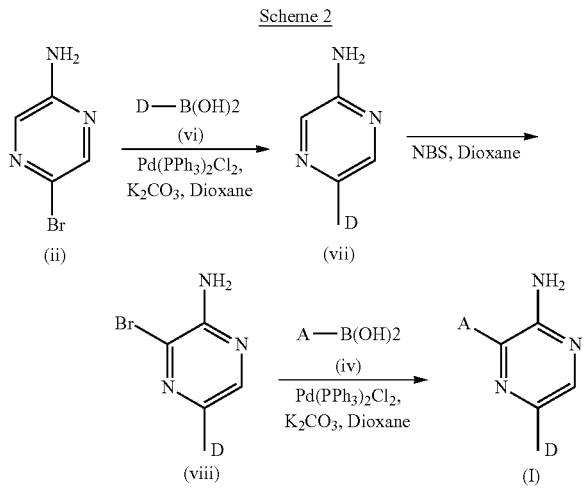

wherein A and D are as defined in Scheme 1.

To a solution of 5-bromo-pyrazine-2-amine according to formula (ii) (2.3 g, 13.21 mmol) in 1,4-dioxane (15 ml) was added a boronic acid of formula (vi) such as 4-methylsulfonylphenylboronic acid (CombiBlocks) (2.77 g, 13.87 mmol) at RT and the resulting mixture was purged with $N_2$ gas for 30 minutes. Bis(triphenylphosphine)palladium(II)chloride (463 mg, 0.66 mmol) and 1 M aqueous solution of potassium carbonate (15.84 ml, pre-purged with $N_2$ gas) were added to the reaction mixture. The reaction mixture was heated to reflux for 16 h, cooled to RT and concentrated under vacuum. 10 ml of water was added to the reaction mixture and extracted with ethyl acetate (15 ml×4). Combined organic layers were washed with brine solution (10 ml), dried over anhydrous $Na_2SO_4$ and concentrated under vacuum. The crude material was purified by column chromatography over silica gel 230-400 mesh by using 2-3% of MeOH in DCM as an eluent to yield to a 5-substituted pyrazine-2-amine of formula (vii) (2.5 g, 75.91%) as white solid. To a solution of compound of formula (vii) (1.5 g, 4.0 mmol) in dry THF (30 ml) was added N-bromosuccinimide (1.58 g, 6.01 mmol) portion-wise at RT and heated to reflux for 30 minutes. Reaction mixture was cooled to RT, added 10 ml of water and extracted with ethyl acetate (30 ml×3). Combined organic layers was washed with brine solution (20 ml), dried over anhydrous $Na_2SO_4$ and concentrated under vacuum. The crude material was purified by column chromatography over silica gel 230-400 mesh by using 40% of ethyl acetate in petroleum ether as an eluent to yield to a 5-substituted-3-bromopyrazine-2-amine of formula (viii) (1.02 g, 67.10%) as white solid.

To a suspension of compound (viii) (330 mg, 1.0 mmol) in 1,4-dioxane (5 ml) was added a boronic acid of formula (iv) such as 4-(trifluoromethyl)phenyl boronic acid (CombiBlocks (200 mg, 1.05 mmol) at RT and the resulting mixture was purged with N$_2$ gas for 30 minutes. Bis(triphenylphosphine)palladium(II)chloride (49 mg, 0.07 mmol) and 1 M aqueous solution of potassium carbonate (1.2 ml, pre-purged with N$_2$ gas) were added to the reaction mixture. The reaction mixture was heated to reflux for 16 h, cooled to RT and concentrated under vacuum. 5 ml of water was added to the reaction mixture and extracted with ethyl acetate (10 ml×4). Combined organic layers were washed with brine solution (5 ml), dried over anhydrous Na$_2$SO$_4$ and concentrated under vacuum. The crude material was purified by preparative HPLC to yield compound of Formula (I) such as compound (2) (95 mg, 22.90%) as white solid.

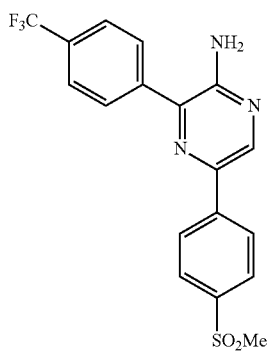

(2)

5-(4-(methylsulfonyl)phenyl)-3-(4-(trifluoromethyl)phenyl)pyrazin-2-amine; MS m/z [M$^+$H]$^+$: 394.0; 400 MHz, DMSO-d6: δ 8.76 (s, 1H), 8.25 (d, J=8.48 Hz, 2H), 8.02 (d, J=8.12 Hz, 2H), 7.97 (d, J=8.48 Hz, 2H), 7.88 (d, J=8.20 Hz, 2H), 6.76 (s, 2H), 3.24 (s, 3H). Compound (3), i.e. 5-(4-(methylsulfonyl)phenyl)-3-(6-(trifluoromethyl)pyridin-3-yl)pyrazin-2-amine was prepared using 2-(trifluoromethyl)pyridine-5-boronic acid pinacol ester in step 3 which gave 0.243 g (25.31%) yield as white solid.

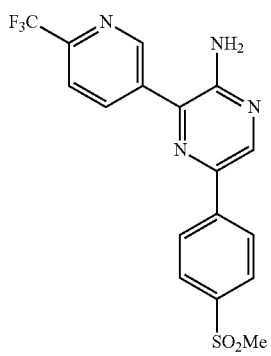

(3)

MS m/z [M+H]+: 395.0; 400 MHz, DMSO-d6: δ 9.15 (d, J=1.72 Hz, 1H), 8.83 (d, J=9.56 Hz, 1H), 8.47 (dd, J=1.80, 8.06 Hz, 1H), 8.28 (d, J=8.64 Hz, 2H), 8.05 (d, J=8.16 Hz, 1H), 7.97-8.00 (m, 2H), 6.94 (s, 2H), 3.25 (s, 3H).

Alternatively, compounds of Formula (I) wherein R$^2$ is —C(O)NR$^{11}$R$^{12}$ and R$^{11}$ and R$^{12}$ are independently selected from H and optionally substituted C$_1$-C$_6$ alkyl or when NR$^{11}$R$^{12}$ forms together an optionally substituted heterocycloalkyl being an optionally substituted morpholino group can be obtained as depicted in Scheme 2 as described below:

Compounds of Formula (I) Wherein R$^2$ is —C(O)NR$^{11}$R$^{12}$ and R$^{11}$ and R$^{12}$ are Independently Selected from H and Optionally Substituted C$_1$-C$_6$ alkyl To a solution of a 5-bromo-pyrazine-2-amine according to formula (ii) (2.3 g, 13.21 mmol) in 1,4-dioxane (15 ml) was added a boronic acid of formula (vi) such as 4-carbamoylphenylboronic acid (CombiBlocks) (2.29 g, 13.87 mmol) at RT and the resulting mixture was purged with N$_2$ gas for 30 minutes. Bis(triphenylphosphine) palladium(II)chloride (462 mg, 0.66 mmol) and 1 M aqueous solution of potassium carbonate (15.84 ml, pre-purged with N$_2$ gas) were added to the reaction mixture. The reaction mixture was heated to reflux for 16 h, cooled to RT and concentrated under vacuum. 10 ml of water was added to the reaction mixture. Precipitate solid was filtered, washed with cold water (2 ml×3), DCM (3 ml×3) and dried to get a 5-substituted pyrazine-2-amine of formula (vii) (2.0 g, 70.82%) as white solid. To a solution of compound (vii) (1 g, 4.66 mmol) in dry 1,4-dioxane (100 ml) was added N-bromosuccinimide (0.83 g, 4.66 mmol) portionwise at RT and the solution was heated to 80° C. for 4 h. Reaction mixture was concentrated under vacuum and water was added (10 ml). Precipitate solid was filtered and dried. The crude solid was purified by column chromatography over silica gel 230-400 mesh by using 2-3% of MeOH in DCM as an eluent to yield 5-substituted 3-bromopyrazine-2-amine of formula (viii) (0.4 g, 29.23%) as white solid. To a suspension of intermediate (viii) (300 mg, 1.02 mmol) in 1,4-dioxane (10 ml) was added a boronic acid of formula (iv) such as 4-(trifluoromethyl)phenyl boronic acid (CombiBlocks) (204 mg, 1.07 mmol) at RT and the resulting mixture was purged with N$_2$ gas for 30 minutes. Bis(triphenylphosphine)palladium(II) chloride (50 mg, 0.07 mmol) and 1 M aqueous solution of potassium carbonate (1.22 ml, pre-purged with N$_2$ gas) were added to the reaction mixture. The reaction mixture was heated to reflux for 16 h, cooled to RT and concentrated under vacuum. 5 ml of water was added to the reaction mixture and extracted with ethyl acetate (10 ml×4). Combined organic layers were washed with brine solution (5 ml), dried over anhydrous Na$_2$SO$_4$ and concentrated under vacuum. The crude solid was purified by column chromatography over silica gel 230-400 mesh by using 1.2-1.5% of MeOH in DCM as an eluent to yield to a compound of Formula (I) such as compound (4) (180 mg, 48.18%) as pale yellow solid.

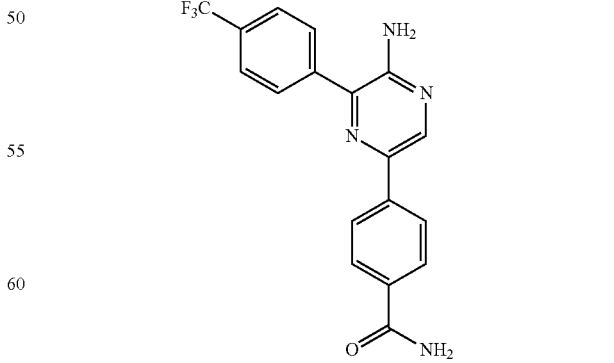

(4)

4-(5-amino-6-(4-(trifluoromethyl)phenyl)pyrazin-2-yl)benzamide; MS m/z [M$^+$H]$^+$: 359.2; 400 MHz, DMSO-d6: δ 8.71 (s, 1H), 8.01-8.08 (m, 5H), 7.94 (d, J=8.40 Hz, 2H), 7.87

(d, J=8.24 Hz, 2H), 7.37 (s, 1H), 6.62 (s, 2H). Compound (5), i.e. 4-(5-amino-6-(6-(trifluoromethyl)pyridin-3-yl)pyrazin-2-yl)benzamide was prepared using 2-(trifluoromethyl)pyridine-5-boronic acid pinacol ester in Step 3 which gave 0.450 g (61.22%) yield as pale yellow solid.

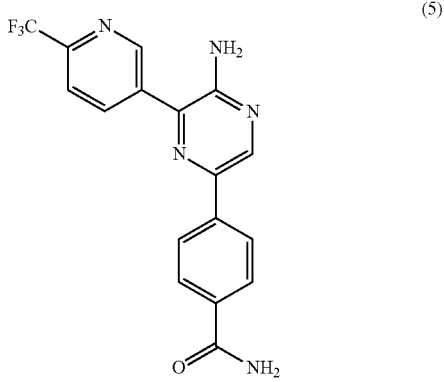 [SMILES: NC(=O)c1ccc(-c2cnc(N)c(-c3ccc(C(F)(F)F)nc3)n2)cc1]

MS m/z [M+H]+: 360.0; 400 MHz, DMSO-d6: δ 9.15 (d, J=1.72 Hz, 1H), 8.75 (s, 1H), 8.47 (dd, J=1.92, 8.06 Hz, 1H), 8.09 (d, J=8.48 Hz, 2H), 8.01-8.04 (m, 2H), 7.95 (d, J=8.52 Hz, 2H), 7.37 (s, 1H), 6.79 (s, 2H).

Compounds of Formula (I) Wherein $R^2$ is —C(O)$NR^{11}R^{12}$ where $NR^{11}R^{12}$ Forms Together an Optionally Substituted Heterocycloalkyl being an Optionally Substituted Morpholino Group To the solution of a 5-bromo-pyrazine-2-amine according to formula (1.5 g, 8.62 mmol) in 1,4-dioxane (20 ml) was added a boronic acid of formula (vi) such as 4-(morpholine-4-carbonyl)phenylboronic acid (CombiBlocks) (2.046 g, 8.70 mmol) at RT and the resulting mixture was purged with $N_2$ gas for 30 minutes. Bis(triphenylphosphine)palladium (II) chloride (423 mg, 0.60 mmol) and 1 M aqueous solution of potassium carbonate (10.34 ml, pre-purged with $N_2$ gas) were added to the reaction mixture. The reaction mixture was heated to reflux for 16 h, cooled to RT and concentrated under vacuum. 5 ml of water was added to the reaction mixture and extracted with ethyl acetate (20 ml×4). Combined organic layers were washed with brine solution (5 ml), dried over anhydrous $Na_2SO_4$ and concentrated under vacuum. The crude material was purified by column chromatography over silica gel 230-400 mesh by using 2% of MeOH in DCM as an eluent to yield a 5-substituted pyrazine-2-amine of formula (vii) (1.1 g, 44.88%) as pale yellow solid. To a suspension of a compound of formula (vii) (1.1 g, 3.86 mmol) in dry DCM (10 ml) was added N-bromosuccinimide (0.688 g, 3.86 mmol) portion-wise under cold condition and the resulting mixture was allowed to stir at RT for 30 minutes. To the reaction mixture was added 5 ml of water and the layers were separated. Aqueous layer was extracted with DCM (10 ml×3). Combined organic layers were washed with brine solution (5 ml), dried over anhydrous $Na_2SO_4$ and concentrated under vacuum. The crude material was purified by column chromatography over silica gel 230-400 mesh by using 3% of MeOH in DCM as an eluent to yield 5-a substituted 3-bromopyrazine-2-amine of formula (viii) (0.85 g, 60.48%) as yellow solid. To a suspension of compound of formula (viii) (825 mg, 1.17 mmol) in 1,4-dioxane (10 ml) was added a boronic acid of formula (iv) such as 4-(trifluoromethyl)phenyl boronic acid (CombiBlocks) (233 mg, 1.22 mmol) at RT and the resulting mixture was purged with $N_2$ gas for 30 minutes. Bis(triphenylphosphine)palladium(II)chloride (58 mg, 0.081 mmol) and 1 M aqueous solution of potassium carbonate (1.46 ml, pre-purged with $N_2$ gas) were added to the reaction mixture. The reaction mixture was heated to reflux for 16 h, cooled to RT and concentrated under vacuum. 5 ml of water was added to the reaction mixture and extracted with ethyl acetate (10 ml×4). Combined organic layers were washed with brine solution (5 ml), dried over anhydrous $Na_2SO_4$ and concentrated under vacuum. The crude material was purified by column chromatography over silica gel 230-400 mesh by using 2% of MeOH in DCM as an eluent to yield to a compound of Formula (I) such as compound (11) (24 mg, 48.87%) as pale off white solid.

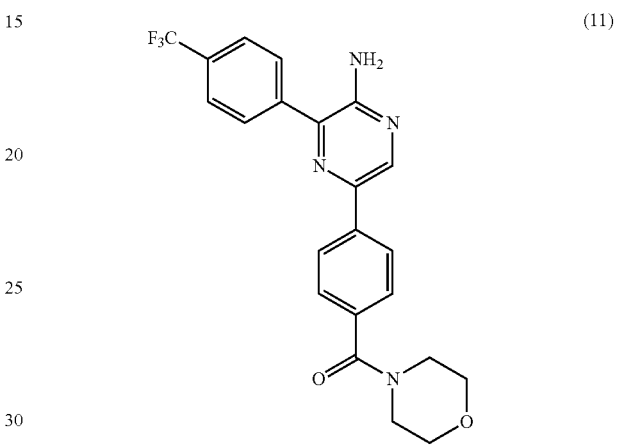

(4-(5-amino-6-(4-(trifluoromethyl)phenyl)pyrazin-2-yl)phenyl)(morpholino)methanone; MS m/z [M+H]+: 429.1; 400 MHz, DMSO-d6: δ 8.67 (s, 1H), 8.02-8.08 (m, 4H), 7.87 (d, J=8.28 Hz, 2H), 7.48 (d, J=8.20 Hz, 2H), 6.61 (s, 2H), 3.63 (br, 8H). Compound (10), i.e. (4-(5-amino-6-(6-(trifluoromethyl)pyridin-3-yl)pyrazin-2-yl)phenyl) (morpholino)methanone was prepared using 2-(trifluoromethyl)pyridine-5-boronic acid pinacol ester in step 4 which gave 0.261 g (51.95%) yield as yellow solid.

MS m/z [M+H]+: 430.2; 400 MHz, DMSO-d6: δ 9.15 (d, J=1.72 Hz, 1H), 8.73 (s, 1H), 8.47 (dd, J=1.80, 8.10 Hz, 1H), 8.03-8.09 (m, 3H), 7.49 (d, J=8.40 Hz, 2H), 6.79 (s, 2H), 3.61 (br, 8H).

Alternatively, compounds of Formula (I) wherein $R^2$ is —C(O)$NR^{11}R^{12}$ and $R^{11}$ and $R^{12}$ are independently selected from H and optionally substituted $C_1$-$C_6$ alkyl or when $NR^{11}R^{12}$ forms together an optionally substituted heterocycloalkyl being an optionally substituted 4-methyl piperazin-1-yl, 4-t-butyl piperazin-1-yl can be obtained as depicted in Scheme 3 below:

Scheme 3

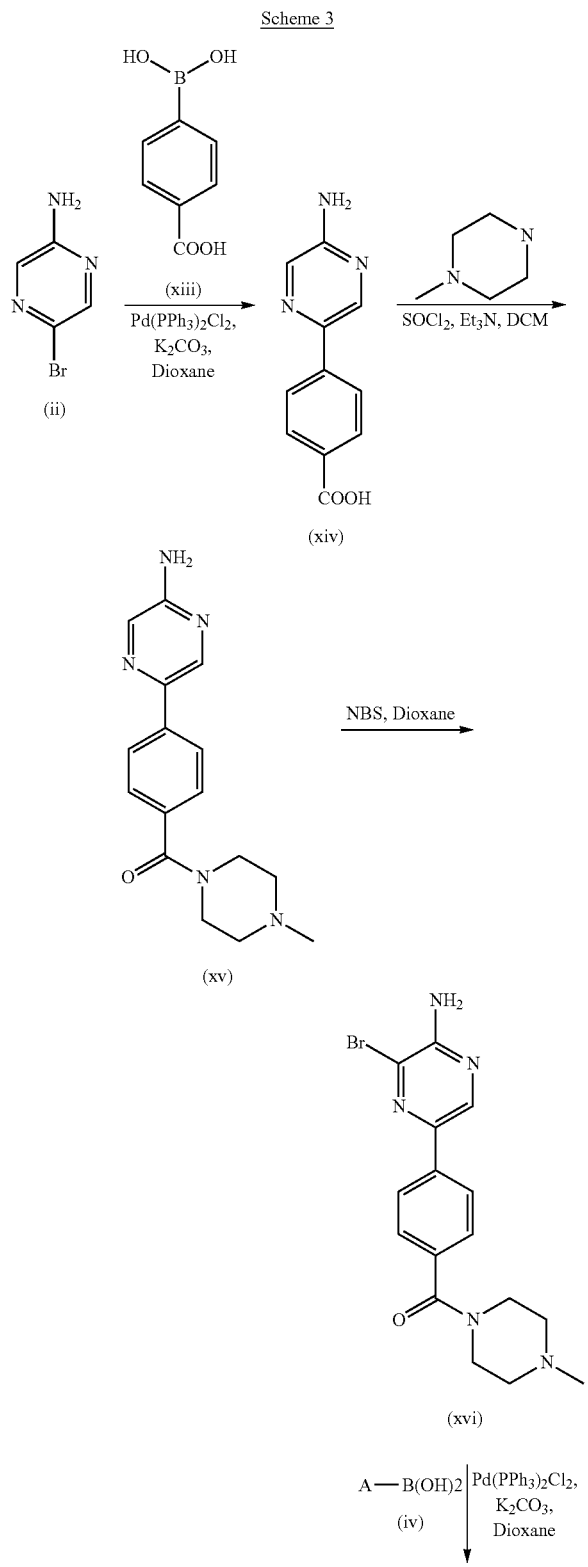

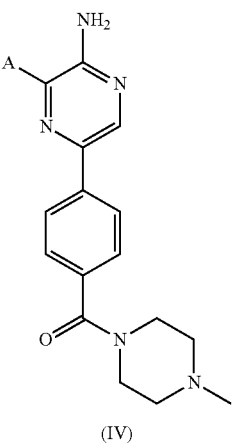

Wherein A is as defined in Scheme 1.

To the solution of a 5-bromo-pyrazine-2-amine according to formula (ii) (8.5 g, 48.8 mmol) in 1,4-dioxane (75 ml) was added 4-carboxyphenylboronic acid (8.45 g, 51.2 mmol) at RT and the resulting mixture was purged with $N_2$ gas for 30 minutes. Bis(triphenylphosphine)palladium(II)chloride (1.71 g, 2.44 mmol) and 1M aqueous solution of potassium carbonate (58.51 ml, pre-purged with $N_2$ gas) were added to the reaction mixture. The reaction mixture was heated to reflux for 16 h, cooled to RT and concentrated under vacuum. The crude material was purified by preparative HPLC to yield a novel carboxylic acid intermediate of formula (xiv) (5.37 g, 51.43%) as solid. To a suspension of a carboxylic acid intermediate of formula (xiv) (1 g, 4.67 mmol) in dry DCM (10 ml) was added thionylchloride (1 ml) under cold condition and refluxed for 2 h. Reaction mixture was concentrated under vacuum in $N_2$-atmosphere and added 10 ml of dry DCM. Reaction mixture was cooled to 0° C., added triethylamine (1.287 g, 12.72 mmol) followed by N-methylpiperazine (425 mg, 4.24 mmol) in DCM (3 ml) and allowed to stir at RT for 6 h. 5 ml of cold water was added to the reaction mixture and the layers were separated. Aqueous layer was extracted with DCM (10 ml×2). Combined organic layers was washed with brine solution (5 ml), dried over anhydrous $Na_2SO_4$ and concentrated under vacuum. The crude material was purified by column chromatography over silica gel 230-400 mesh by using 2-3% of MeOH in DCM as an eluent to yield to a novel ketone intermediate of formula (xv) (660 mg, 52.38%) as solid. To a solution of an amide intermediate of formula (xv) (1 g, 4.01 mmol) in dry 1,4-dioxane (10 ml) was added N-bromosuccinimide (1.07 g, 6.02 mmol) portion-wise at RT and the resulting mixture was allowed to stir for 30 minutes. Reaction mixture was decanted and dried to yield crude intermediate of formula (xvi) (0.5 g) as gummy solid. To the suspension of crude (xvi) (250 mg, 0.66 mmol) in 1,4-dioxane (4 ml) was added a boronic acid of formula (iv) such as 4-(trifluoromethyl)phenyl boronic acid (CombiBlocks) (0.69 mmol) at RT and purged with $N_2$ gas for 30 minutes. Bis(triphenylphosphine)palladium(II)chloride (32 mg, 0.46 mmol) and 1 M aqueous solution of potassium carbonate (0.79 ml, pre-purged with $N_2$ gas) were added to the reaction mixture. The reaction mixture was heated to reflux for 16 h, cooled to RT and concentrated under vacuum. 3 ml of water was added to the reaction mixture and extracted with ethyl acetate (10 ml×4). Combined organic layers was washed with brine solution (5 ml), dried over anhydrous $Na_2SO_4$ and concentrated under vacuum. The crude solid was purified by column chromatography over silica gel 230-400 mesh by using 2-3% of MeOH in DCM as an eluent to yield to a compound of Formula (I) such as a compound of Formula (iv) like for example compound (6) (20 mg, 6.87%) as solid.

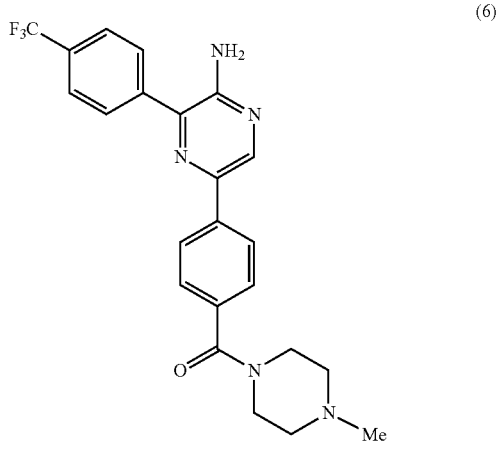 [SMILES: CN1CCN(C(=O)c2ccc(-c3cnc(N)c(-c4ccc(C(F)(F)F)cc4)n3)cc2)CC1]

(6)

(4-(5-amino-6-(4-(trifluoromethyl)phenyl)pyrazin-2-yl)phenyl)(4-methylpiperazin-1-yl) methanone; MS m/z [M+H]+: 442.2; 400 MHz, CDCl3: δ 8.55 (s, 1H), 7.98-8.04 (m, 4H), 7.82 (d, J=8.00 Hz, 2H), 7.53 (d, J=8.00 Hz, 2H), 4.89 (s, 2H), 3.74 (d, J=125.20 Hz, 4H), 2.60 (bs, 4H), 2.41 (s, 3H). Compound (7), i.e. (4-(5-amino-6-(6-(trifluoromethyl)pyridin-3-yl)pyrazin-2-yl)phenyl)(4-methylpiperazin-1-yl) methanone was prepared using 2-(trifluoromethyl)pyridine-5-boronic acid pinacol ester (CombiBlocks) in step 4 which gave 17.9 mg (6.16%) yield as solid.

(7)

MS m/z [M+H]+: 443.2; 400 MHz, CDCl3: δ 9.26 (d, J=1.60 Hz, 1H), 8.60 (s, 1H), 8.40 (dd, J=1.60, 8.00 Hz, 1H), 8.03 (d, J=8.00 Hz, 2H), 7.88 (d, J=8.00 Hz, 1H), 7.53 (d, J=8.40 Hz, 2H), 4.90 (s, 2H), 3.90 (s, 2H), 3.58 (s, 2H), 2.61 (s, 2H), 2.47 (s, 2H), 2.42 (s, 3H).

Alternatively, compounds of Formula (I) wherein $R^2$ is —C(O)NR$^{11}$R$^{12}$ and R$^{11}$ and R$^{12}$ are independently selected from H and optionally substituted $C_1$-$C_6$ alkyl or when NR$^{11}$R$^{12}$ forms together an optionally substituted heterocycloalkyl being an optionally substituted piperazin-1-yl can be obtained as depicted in Scheme 4 below:

Scheme 4

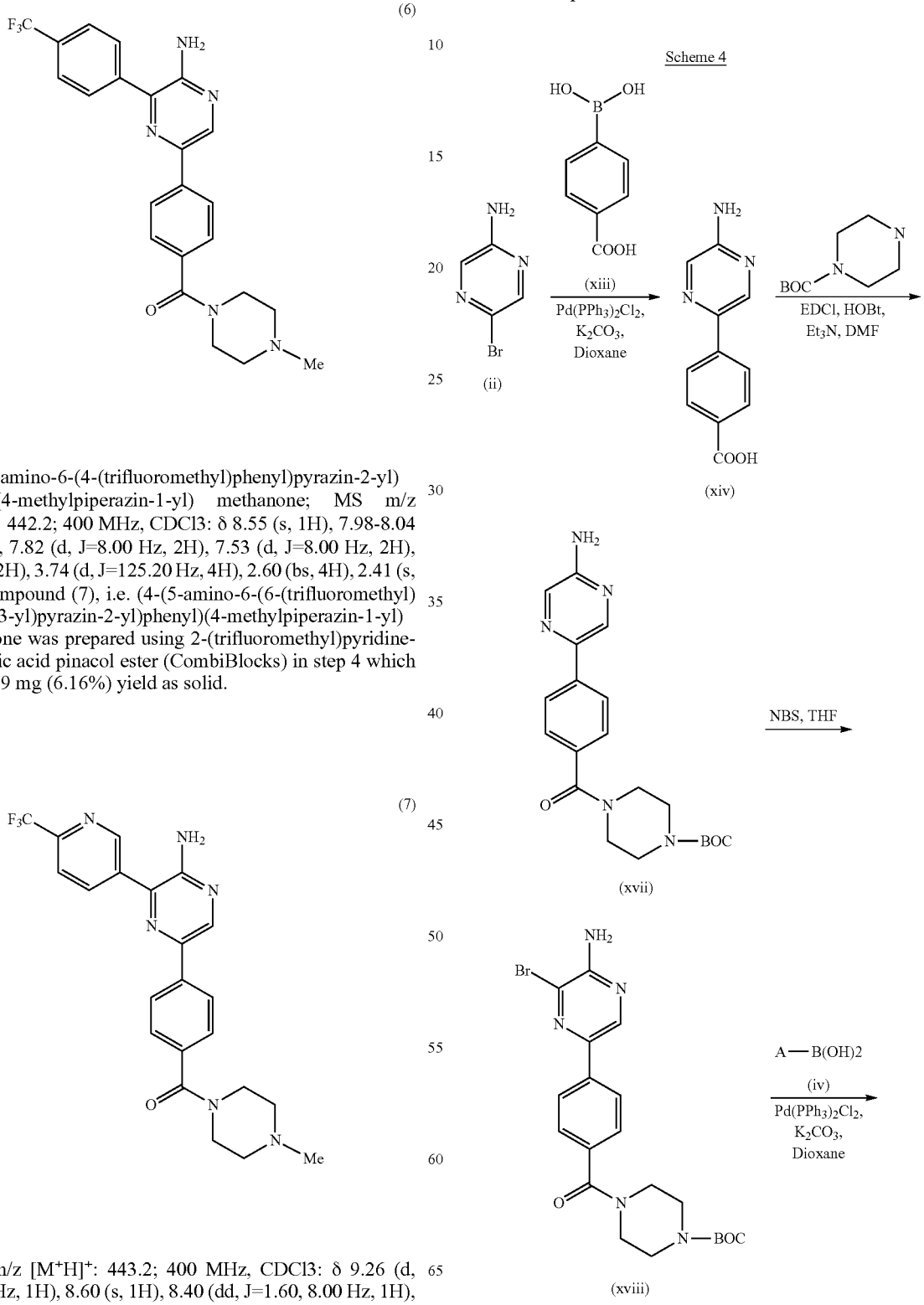

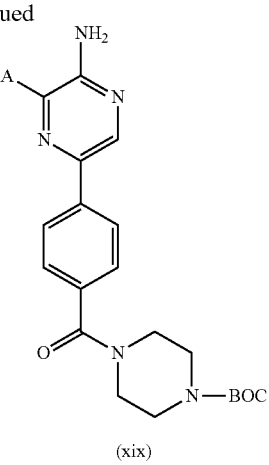

(xix)

↓ TFA, DCM

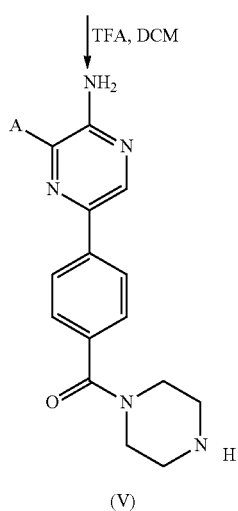

(V)

Wherein A is as defined in Scheme 1.

To the solution of a 5-bromo-pyrazine-2-amine according to formula (ii) (8.5 g, 48.8 mmol) in 1,4-dioxane (75 ml) was added 4-carboxyphenylboronic acid (CombiBlocks) (8.45 g, 51.2 mmol) at RT and the resulting mixture was purged with $N_2$ gas for 30 minutes. Bis(triphenylphosphine)palladium(II) chloride (1.71 g, 2.44 mmol) and 1 M aqueous solution of potassium carbonate (58.51 ml, pre-purged with $N_2$ gas) were added to the reaction mixture. The reaction mixture was heated to reflux for 16 h, cooled to RT and concentrated under vacuum. The crude material was purified by preparative HPLC to yield a carboxylic acid intermediate of formula (xiv) (5.37 g, 51.43%) as solid. To a solution of a carboxylic acid intermediate of formula (xiv) (2.93 g, 13.60 mmol) in dry DMF (15 ml) was added EDCI (3.54 g, 18.54 mmol), HOBt (0.166 g, 1.23 mmol) and triethyl amine (3.75 g, 37.09 mmol) at RT and the solution was allowed to stir for 30 minutes. To the reaction mixture was added N-Boc piperazine (Aldrich) (2.3 g, 12.36 mmol) at RT and the mixture was stirred for 2 h. 25 ml of water was added to the reaction mixture and extracted with ethyl acetate (25 ml×4). Combined organic layers were concentrated under vacuum. To the crude material was added DCM:Petroleum.ether (100 ml, 95:5) and filtered to yield a novel amide intermediate of formula (xvii) (1.02 g, 21.51%) as yellow solid. To the solution of intermediate of formula (xvii) (1 g, 2.60 mmol) in dry THF (25 ml) was added N-bromosuccinimide (0.696 g, 3.91 mmol) portion-wise at RT and the mixture was heated to reflux for 30 minutes. Reaction mixture was cooled to RT, added water (25 ml) and extracted with ethyl acetate (50 ml×3). Combined organic layers were washed with brine solution (20 ml), dried over anhydrous $Na_2SO_4$ and concentrated under vacuum. To the crude solid was added DCM:Pet.ether (50 ml, 95:5) and filtered to yield to a novel intermediate (xviii) (1 g, 83.26%) as brown solid. To the suspension of intermediate (xviii) (400 mg, 0.86 mmol) in 1,4-dioxane (10 ml) was added a boronic acid of formula (iv) such as 4-(trifluoromethyl)phenyl boronic acid (CombiBlocks) (0.90 mmol) at RT and the u) solution was purged with $N_2$ gas for 30 minutes. Bis(triphenylphosphine) palladium(II)chloride (42 mg, 0.06 mmol) and 1M aqueous solution of potassium carbonate (1.03 ml, pre-purged with $N_2$ gas) were added to the reaction mixture. The reaction mixture was heated to reflux for 16 h, cooled to RT and concentrated under vacuum. 5 ml of water was added to the reaction mixture and extracted with ethyl acetate (20 ml×4). Combined organic layers was washed with brine solution (10 ml), dried over anhydrous $Na_2SO_4$ and concentrated under vacuum. The crude solid was purified by column chromatography over silica gel 230-400 mesh by using 50% of ethyl acetate in petroleum.ether as an eluent yield intermediate (xix) wherein A is para-trifluoromethyl phenyl (205 mg, 44.95%) as yellow solid.

Intermediate (xix) wherein A is para-trifluoromethyl pyridin was prepared using 2-(trifluoromethyl)pyridine-5-boronic acid pinacol ester in step 4 which gave 0.212 g (46.69%) yield as solid.

To the solution of intermediate (xix) (200 mg, 0.37 mml) in DCM (4 ml) was added TFA (0.58 ml, 7.58 mmol) under cold condition and the resulting mixture was allowed to stir at RT for 45 minutes. Reaction mixture was concentrated under vacuum and crude was washed with diethyl ether (1.5 ml×4) and dried. Reaction mixture was dissolved in dry DCM:MeOH (10 ml, 9:1), added Amberlyst A21 (0.157 mg, 0.75 mmol) at RT and allowed to stir for 30 minutes. Reaction mixture was filtered, washed with DCM:MeOH (3 ml×3, 9:1) and filtrate was concentrated under vacuum. Crude compound was triturated with Diethylether (1.5 ml×5) and dried to yield to a compound of Formula (I), such as compound (8) (90 mg, 55.55%) as yellow solid.

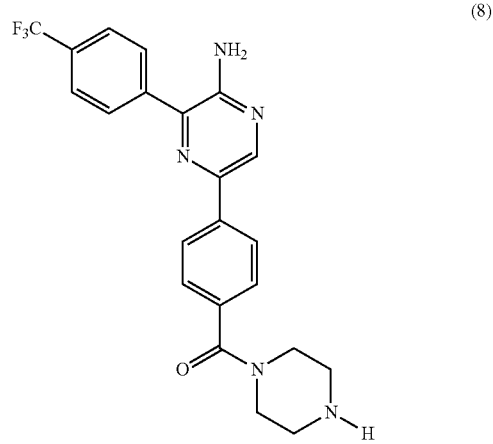 [SMILES: Nc1ncc(-c2ccc(C(=O)N3CCNCC3)cc2)nc1-c1ccc(C(F)(F)F)cc1]

(8)

(4-(5-amino-6-(4-(trifluoromethyl)phenyl)pyrazin-2-yl) phenyl)(piperazin-1-yl)methanone; MS m/z [M+H]+: 428.2; 400 MHz, DMSO-d6: δ 8.68 (s, 1H), 8.03-8.08 (m, 4H), 7.88 (d, J=8.08 Hz, 2H), 7.47 (d, J=8.16 Hz, 2H), 6.62 (s, 2H), 3.55 (d, J=25.40 Hz, 4H), 2.79 (s, 4H). Compound (9), i.e. (4-(5-amino-6-(6-(trifluoromethyl)pyridin-3-yl)pyrazin-2-yl)phenyl)(piperazin-1-yl) methanone was prepared following the same protocol but using intermediate (xix) wherein A is para-trifluoromethyl pyridin which gave 0.132 g (81.48%) yield as white solid.

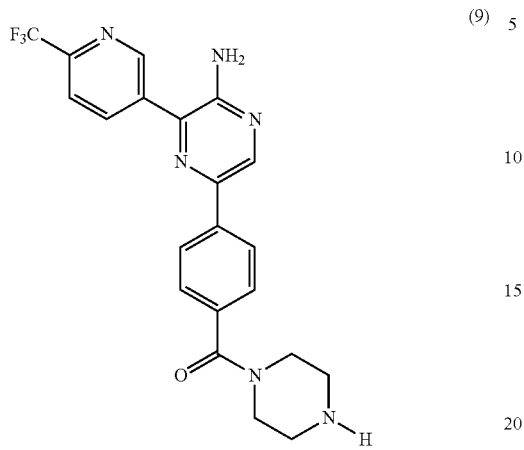

(9)

MS m/z [M+H]+: 429.2; 400 MHz, DMSO-d6: δ 9.15 (s, 1H), 8.74 (s, 1H), 8.47 (d, J=8.16 Hz, 1H), 8.10 (d, J=8.32 Hz, 2H), 8.05 (d, J=8.16 Hz, 1H), 7.52 (d, J=8.36 Hz, 2H), 6.81 (s, 2H), 3.59 (bs, 4H), 3.04 (s, 4H).

Alternatively, compounds of Formula (I) wherein $R^2$ is —C(O)NR$^{11}$R$^{12}$ and R$^{11}$ and R$^{12}$ are independently selected from H and optionally substituted $C_1$-$C_6$ alkyl or when NR$^{11}$R$^{12}$ forms together an optionally substituted heterocycloalkyl being an optionally substituted diazepan (e.g. 1,4 diazepan, 4-methyl 1,4 diazepan), optionally substituted pyrrolidin (e.g. 3-hydroxy pyrrolidin-1-yl, 3-amino pyrrolidin-1-yl), optionally substituted piperidine (e.g. 4-hydroxy piperidin-1-yl, 4-amino piperidin-1-yl) can be obtained as depicted in Scheme 5 below:

Scheme 5

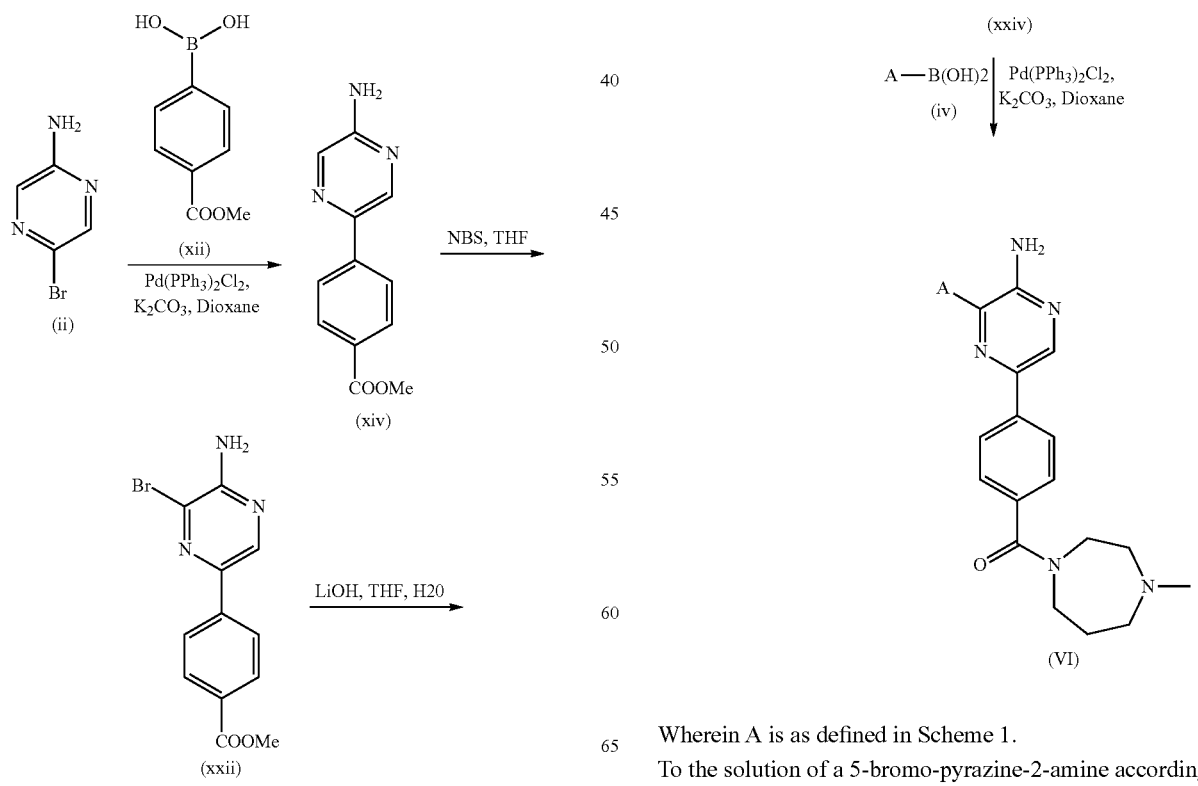

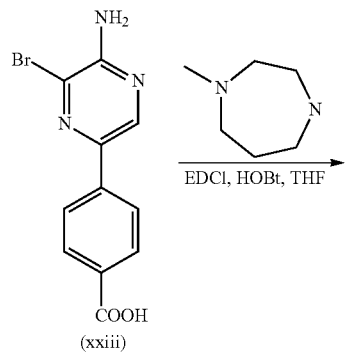

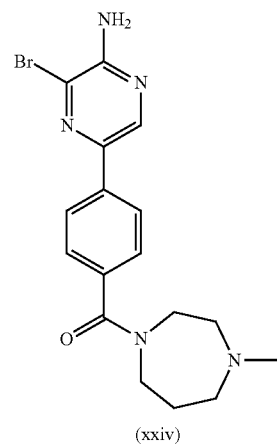

Wherein A is as defined in Scheme 1.

To the solution of a 5-bromo-pyrazine-2-amine according to formula (ii) (10 g, 57.47 mmol) in 1,4-dioxane (100 ml)

was added 4-methoxycarbonylphenylboronic acid (11.377 g, 63.21 mmol) followed by potassium phosphate tribasic (14.638 g, 68.96 mmol) and water 68.96 ml at RT. Reaction mixture was purged with N$_2$ gas for 1 h. Bis(triphenylphosphine)palladium(II)chloride (2.823 g, 4.02 mmol) was added to the reaction mixture. The reaction mixture was heated to reflux for 16 h, cooled to RT and to concentrated under vacuum to remove dioxane. Solid was filtered, washed with water (20 ml×3), dried and again washed with MeOH (10 ml×4) and dried to afford compound a methyl carboxylate intermediate of formula (xiv) (12.035 g, 91.36%, 84% purity) as pale yellow solid. To a cold suspension of a methyl carboxylate intermediate of formula (xiv) (7.5 g, 32.71 mmol) in dry DCM (75 ml) was added N-bromosuccinimide (6.405 g, 35.99 mmol) portion-wise and the resulting mixture was stirred at RT for 1 h. To the reaction mixture was added 20 ml of water. The solution was extracted with DCM:MeOH (100 ml×5). Combined organic layers were washed with brine solution (50 ml), dried over anhydrous Na$_2$SO$_4$ and concentrated under vacuum. Crude material was purified by column chromatography over silica gel 230-400 mesh by using 24% of ethyl acetate and 4% of DCM in petroleum ether as an eluent to afford a novel intermediate of formula (xxii) 4.767 g, 47.28%) as pale yellow solid. To a solution of compound an intermediate of formula (xxii) (4.76 g, 15.44 mmol) in THF (50 ml) was added lithium hydroxide [0.554 g, 23.17 mmol, in water (5 ml)] at RT. The resulting mixture was stirred for 16 h and concentrated under vacuum. To the residue was added 10 ml of water and conc. HCl till acidic. Solid was filtered, washed with water (10 ml×3), dried and again washed with DCM (10 ml×3) and dried to get a novel intermediate compound of formula (xxiii) (4.102 g, 90.33%) as pale yellow solid. To a suspension of an intermediate compound of formula (xxiii) (600 mg, 2.04 mmol) in dry THF (12 ml) was added EDCI-HCl (469 mg, 72.44 mmol), HOBt (28 mg, 0.20 mmol) and triethyl amine (516 mg, 5.10 mmol) at RT under N$_2$ atmosphere and the resulting mixture was stirred for 1 h. 1-methylhomo piperazine (256 mg, 2.24 mmol) was then added at RT and the solution was stirred for 16 h. 20 ml of water was added to the reaction mixture and extraction was carried out with ethyl acetate (50 ml×4). Combined organic layers was washed with brine solution (20 ml), dried over anhydrous Na$_2$SO$_4$ and concentrated under vacuum. The crude material was purified by column chromatography over neutral alumina by using 12% of MeOH in DCM as an eluent to yield to a novel intermediate compound of formula (xxiv) (350 mg, 43.96%) as pale yellow solid. To a solution of compound intermediate compound of formula (xxiv) (350 mg, 0.89 mmol) in 1,4-dioxane (5 ml) was added a boronic acid of formula (vi) such as 2-(trifluoromethyl)pyridine-5-boronic acid pinacol ester (CombiBlocks) (269 mg, 0.98 mmol) at RT and purged with N$_2$ gas for 30 minutes. Bis (triphenylphosphine) palladium(II)chloride (45 mg, 0.062 mmol) and 1 M aqueous solution of potassium carbonate (1.07 ml, 1.07 mmol, pre-purged with N$_2$ gas) were added to the reaction mixture. The reaction mixture was heated to reflux for 16 h, cooled to RT and concentrated under vacuum. 3 ml of brine solution was added to the reaction mixture and extracted with ethyl acetate (10 ml×4). Combined organic layers was dried over anhydrous Na$_2$SO$_4$ and concentrated under vacuum. The crude material was purified by column chromatography over silica gel 230-400 mesh by using 5-6% of MeOH in DCM as an eluent to afford a compounds of Formula (I) such as compound (12) (250 mg, 61.12%) as pale yellow solid.

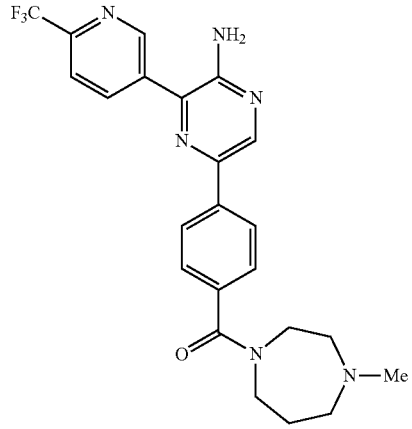

(12)

(4-(5-amino-6-(6-(trifluoromethyl)pyridin-3-yl)pyrazin-2-yl)phenyl)(4-methyl-1,4-diazepan-1-yl)methanone; MS m/z [M$^+$H]$^+$: 457.2; 400 MHz, DMSO-d6: δ 9.15 (s, 1H), 8.72 (s, 1H), 8.47 (d, J=8.12 Hz, 1H), 8.03-8.08 (m, 3H), 7.45-7.47 (m, 2H), 6.77 (s, 2H), 3.61-3.67 (m, 2H), 3.40-3.43 (m, 2H), 2.70 (bs, 1H), 2.59 (bs, 2H), 2.27-2.35 (m, 3H), 1.88 (bs, 1H), 1.78 (bs, 1H).

If the above synthetic methods are not applicable to obtain aminopyrazine derivatives according to the invention and/or necessary intermediates, suitable methods of preparation known by a person skilled in the art should be used. In general, the synthesis pathways for any individual derivative will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, 2005 and Theodora W. Greene and Peter G. M. Wuts in "*Protective Groups in Organic Synthesis*", Wiley Interscience, 4$^{th}$ Edition 2006. Compounds of this invention can be isolated in association with solvent molecules by crystallization from evaporation of an appropriate solvent. The pharmaceutically acceptable acid addition salts of the aminopyrazine derivatives, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of an aminopyrazine derivative with a suitable base. Both types of salts may be formed or interconverted using ion-exchange resin techniques.

Example 2

Synthesis of Further Compounds of the Invention

The following compounds listed in Table 1 below were prepared using an analogous procedure to procedure described in Example 1.

TABLE 1

| Compound | Chemical name | Structure | MS m/z [M + H]+ |
|---|---|---|---|
| 13 | 4-(5-amino-6-(3-fluoro-4-(trifluoromethyl)phenyl)pyrazin-2-yl)benzamide | 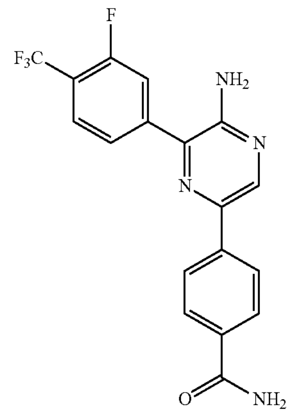 [SMILES: NC(=O)c1ccc(-c2cnc(N)c(-c3ccc(C(F)(F)F)c(F)c3)n2)cc1] | 376.1 |
| 14 | 4-(5-amino-6-(4-(methylsulfonyl)phenyl)pyrazin-2-yl)benzamide | 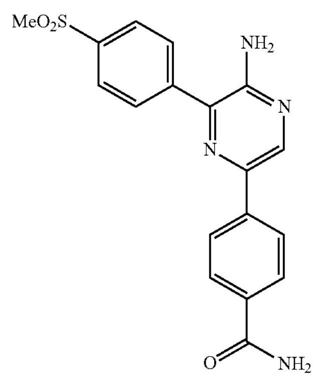 [SMILES: CS(=O)(=O)c1ccc(-c2nc(-c3ccc(C(N)=O)cc3)cnc2N)cc1] | 367.9 |
| 15 | 4,4'-(3-aminopyrazine-2,6-diyl)dibenzamide | 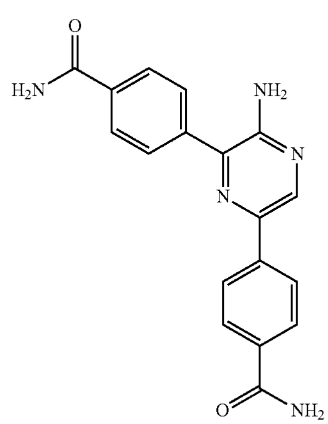 [SMILES: NC(=O)c1ccc(-c2cnc(N)c(-c3ccc(C(N)=O)cc3)n2)cc1] | 332.9 |

TABLE 1-continued

| Compound | Chemical name | Structure | MS m/z [M + H]+ |
|---|---|---|---|
| 16 | 4-(3-amino-6-(4-carbamoyl-phenyl)pyrazin-2-yl)-N-methyl-benzamide | 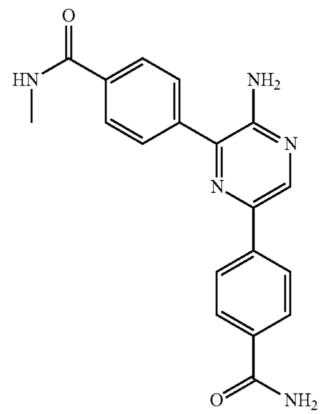 [SMILES: CNC(=O)c1ccc(-c2nc(-c3ccc(C(N)=O)cc3)cnc2N)cc1] | 347.1 |
| 17 | 4-(5-amino-6-(6-(trifluoro-methyl)pyridin-3-yl)pyrazin-2-yl)-N-methylbenzenesulfonamide | 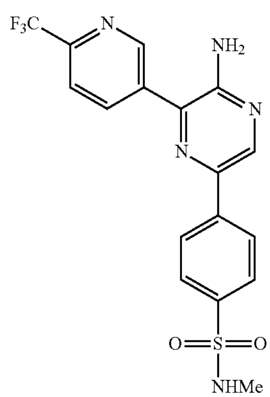 [SMILES: CNS(=O)(=O)c1ccc(-c2cnc(N)c(-c3ccc(C(F)(F)F)nc3)n2)cc1] | 409.1 |
| 18 | 5-(4-(ethylsulfonyl)phenyl)-3-(6-(trifluoromethyl)pyridin-3-yl)pyrazin-2-amine | 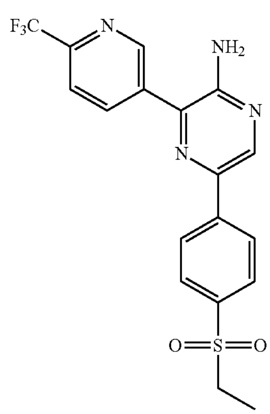 [SMILES: CCS(=O)(=O)c1ccc(-c2cnc(N)c(-c3ccc(C(F)(F)F)nc3)n2)cc1] | 408.1 |

TABLE 1-continued

| Compound | Chemical name | Structure | MS m/z [M + H]+ |
|---|---|---|---|
| 19 | 5-(4-(isopropylsulfonyl)phenyl)-3-(6-(trifluoromethyl)pyridin-3-yl)pyrazin-2-amine | 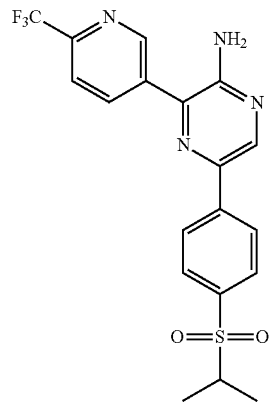 [SMILES: CC(C)S(=O)(=O)c1ccc(-c2cnc(N)c(-c3ccc(C(F)(F)F)nc3)n2)cc1] | 422.0 |
| 20 | (4-(5-amino-6-(4-(trifluoromethyl)phenyl)pyrazin-2-yl)phenyl)(4-tert-butylpiperazin-1-yl)methanone | 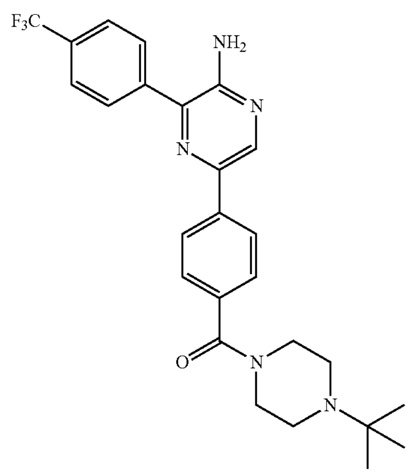 [SMILES: CC(C)(C)N1CCN(C(=O)c2ccc(-c3cnc(N)c(-c4ccc(C(F)(F)F)cc4)n3)cc2)CC1] | 484.4 |
| 21 | (4-(5-amino-6-(4-(trifluoromethyl)phenyl)pyrazin-2-yl)phenyl)(3-hydroxypyrrolidin-1-yl)methanone | 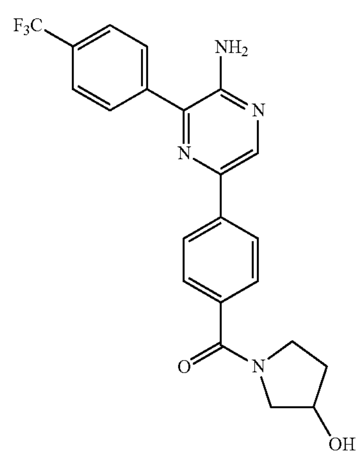 [SMILES: Nc1ncc(-c2ccc(C(=O)N3CCC(O)C3)cc2)nc1-c1ccc(C(F)(F)F)cc1] | 429.2 |

TABLE 1-continued

| Compound | Chemical name | Structure | MS m/z [M + H]+ |
|---|---|---|---|
| 22 | (4-(5-amino-6-(6-(trifluoromethyl)pyridin-3-yl)pyrazin-2-yl)phenyl)(4-hydroxypiperidin-1-yl)methanone | 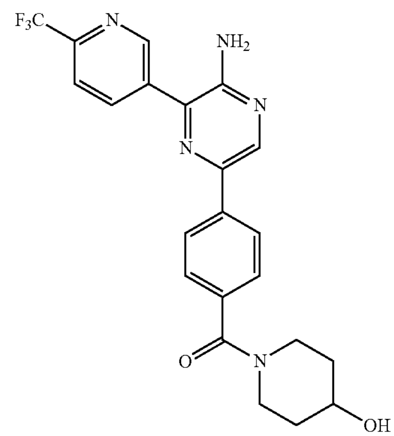 [SMILES: Nc1ncc(-c2ccc(C(=O)N3CCC(O)CC3)cc2)nc1-c1ccc(C(F)(F)F)nc1] | 444.2 |
| 23 | (4-(5-amino-6-(4-(trifluoromethyl)phenyl)pyrazin-2-yl)phenyl)(4-hydroxypiperidin-1-yl)methanone | 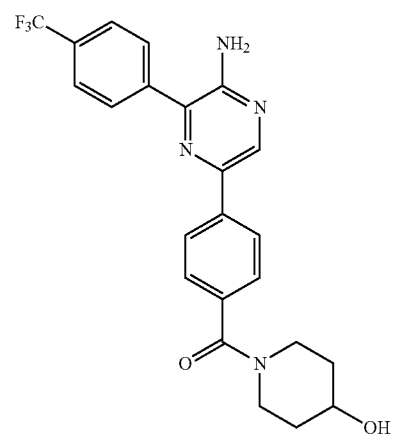 [SMILES: Nc1ncc(-c2ccc(C(=O)N3CCC(O)CC3)cc2)nc1-c1ccc(C(F)(F)F)cc1] | 443.2 |
| 24 | (4-(5-amino-6-(6-(trifluoromethyl)pyridin-3-yl)pyrazin-2-yl)phenyl)(4-(tert-butyl)piperazin-1-yl)methanone | 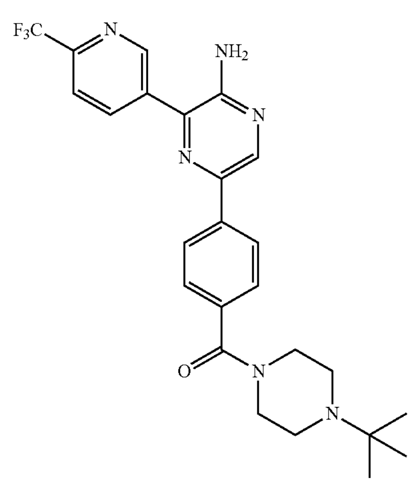 [SMILES: CC(C)(C)N1CCN(C(=O)c2ccc(-c3cnc(N)c(-c4ccc(C(F)(F)F)nc4)n3)cc2)CC1] | 485.5 |

TABLE 1-continued

| Compound | Chemical name | Structure | MS m/z [M + H]+ |
|---|---|---|---|
| 25 | (4-(5-amino-6-(4-(trifluoromethyl)phenyl)pyrazin-2-yl)phenyl)(4-methyl-1,4-diazepan-1-yl)methanone | 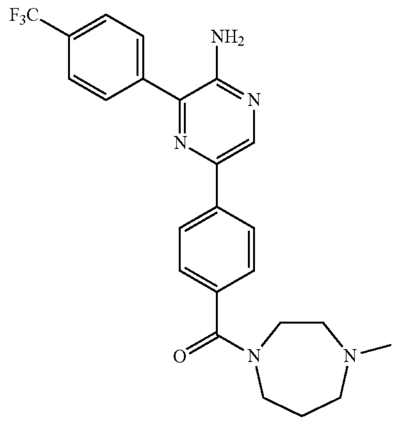 [SMILES: CN1CCCN(C(=O)c2ccc(-c3cnc(N)c(-c4ccc(C(F)(F)F)cc4)n3)cc2)CC1] | 456.2 |
| 26 | (4-(5-amino-6-(6-(trifluoromethyl)pyridin-3-yl)pyrazin-2-yl)phenyl)(1,4-diazepan-1-yl)methanone | 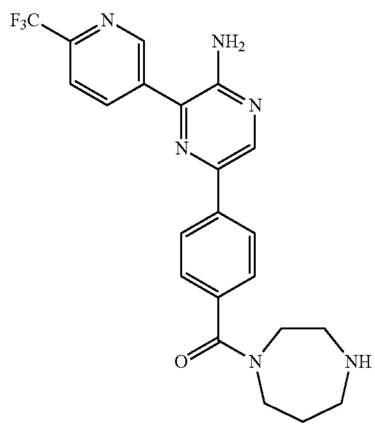 [SMILES: Nc1ncc(-c2ccc(C(=O)N3CCCNCC3)cc2)nc1-c1ccc(C(F)(F)F)nc1] | 443.0 |
| 27 | (4-(5-amino-6-(4-(trifluoromethyl)phenyl)pyrazin-2-yl)phenyl)(1,4-diazepan-1-yl)methanone | 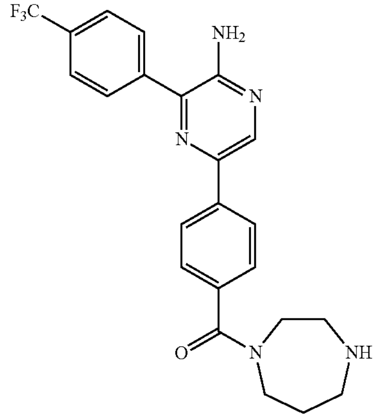 [SMILES: Nc1ncc(-c2ccc(C(=O)N3CCCNCC3)cc2)nc1-c1ccc(C(F)(F)F)cc1] | 442.2 |

TABLE 1-continued

| Compound | Chemical name | Structure | MS m/z [M + H]+ |
|---|---|---|---|
| 28 | (4-(5-amino-6-(6-(trifluoromethyl)pyridin-3-yl)pyrazin-2-yl)phenyl)(3-aminopyrrolidin-1-yl)methanone | 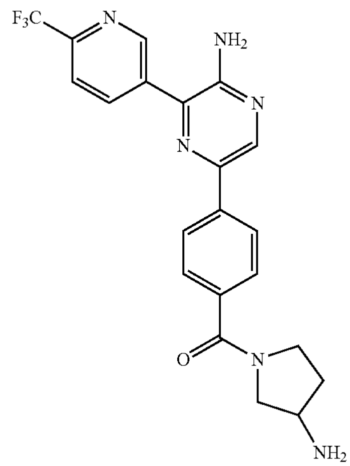 [SMILES: Nc1ncc(-c2ccc(C(=O)N3CCC(N)C3)cc2)nc1-c1ccc(C(F)(F)F)nc1] | 429.0 |
| 29 | (4-(5-amino-6-(4-(trifluoromethyl)phenyl)pyrazin-2-yl)phenyl)(3-aminopyrrolidin-1-yl)methanone | 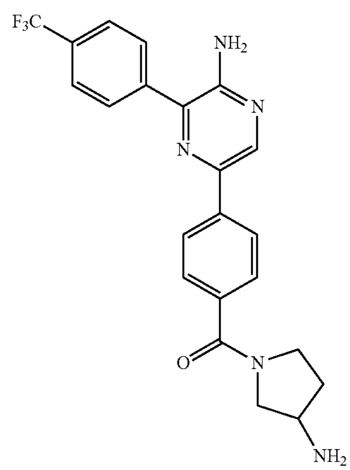 [SMILES: Nc1ncc(-c2ccc(C(=O)N3CCC(N)C3)cc2)nc1-c1ccc(C(F)(F)F)cc1] | 428.0 |
| 30 | (4-(5-amino-6-(6-(trifluoromethyl)pyridin-3-yl)pyrazin-2-yl)phenyl)(3-hydroxypyrrolidin-1-yl)methanone | 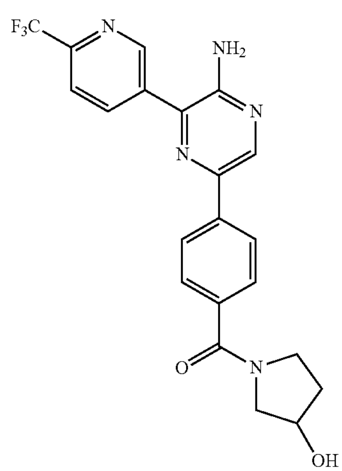 [SMILES: Nc1ncc(-c2ccc(C(=O)N3CCC(O)C3)cc2)nc1-c1ccc(C(F)(F)F)nc1] | 430.2 |

TABLE 1-continued

| Compound | Chemical name | Structure | MS m/z [M + H]+ |
|---|---|---|---|
| 31 | (4-(5-amino-6-(6-(trifluoromethyl)pyridin-3-yl)pyrazin-2-yl)phenyl)(4-aminopiperidinyl)methanone | 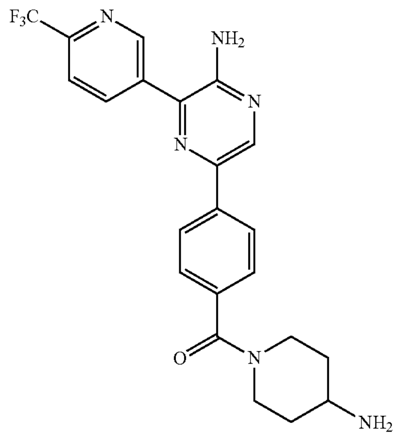 [SMILES: Nc1ncc(-c2ccc(C(=O)N3CCC(N)CC3)cc2)nc1-c1ccc(C(F)(F)F)nc1] | 443.2 |
| 32 | (4-(5-amino-6-(4-(trifluoromethyl)phenyl)pyrazin-2-yl)phenyl)(4-aminopiperidinyl)methanone | 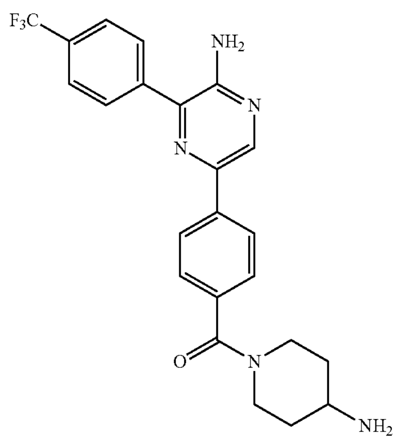 [SMILES: Nc1ncc(-c2ccc(C(=O)N3CCC(N)CC3)cc2)nc1-c1ccc(C(F)(F)F)cc1] | 442.2 |
| 33 | 5-(4-(cyclopropylmethylsulfonyl)phenyl)-3-(6-(trifluoromethyl)pyridin-3-yl)pyrazin-2-amine | 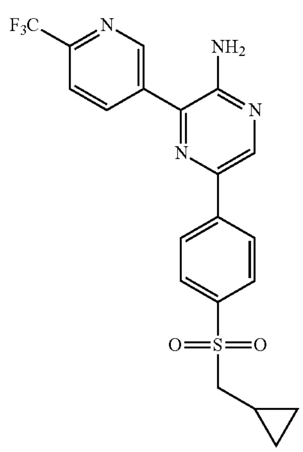 [SMILES: Nc1ncc(-c2ccc(S(=O)(=O)CC3CC3)cc2)nc1-c1ccc(C(F)(F)F)nc1] | 435.0 |

TABLE 1-continued

| Compound | Chemical name | Structure | MS m/z [M + H]+ |
|---|---|---|---|
| 34 | 5-(4-(cyclopropylsulfonyl)phenyl)-3-(6-(trifluoromethyl)pyridin-3-yl)pyrazin-2-amine | 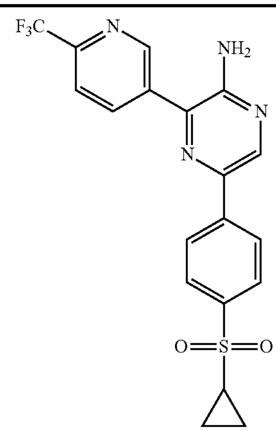 | 421.2 |
| 35 | (R)-(4-(5-amino-6-(4-(trifluoromethyl)phenyl)pyrazin-2-yl)phenyl)(3-hydroxypyrrolidin-1-yl)methanone | 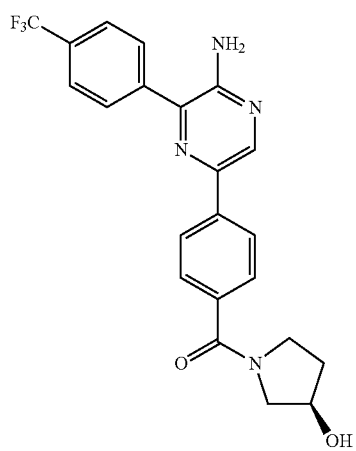 [SMILES: Nc1ncc(-c2ccc(C(=O)N3CC[C@@H](O)C3)cc2)nc1-c1ccc(C(F)(F)F)cc1] | 429.0 |
| 36 | (S)-(4-(5-amino-6-(4-(trifluoromethyl)phenyl)pyrazin-2-yl)phenyl)(3-hydroxypyrrolidin-1-yl)methanone | 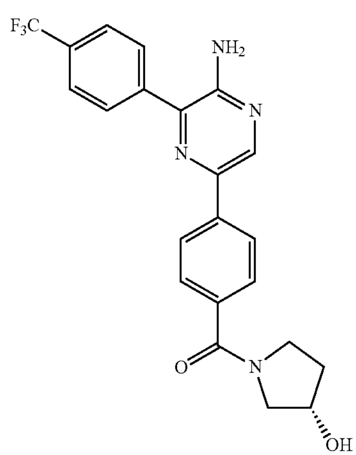 [SMILES: Nc1ncc(-c2ccc(C(=O)N3CC[C@H](O)C3)cc2)nc1-c1ccc(C(F)(F)F)cc1] | 429.0 |

Compounds 13 to 19 and 20 to 32 were synthesized according to schemes 1 and 5, respectively. Compounds 33 and 34 were synthesized according to scheme 1. The separate enantiomer compounds 35 and 36 were obtained after chiral HPLC separation [using a Chiral Pak IA (250×4.6) mm 5 u; Mobile Phase of 0.1% DEA in Hexane: Ethanol (40:60) at a flow rate of 1.0 mL/min] of the mixture, compound 21 which was synthesized according to scheme 3.

The starting material generically described in the reaction schemes which were used to synthesized compounds of the Examples are listed in Table 2 below:

TABLE 2
| Intermediate's formula | Chemical name | Structure |
|---|---|---|
| (iv) | 6-methoxypyridin-3-ylboronic acid | 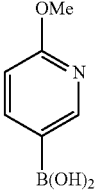 |
| (iv) | 6-(trifluoromethyl)pyridin-3-ylboronic acid | 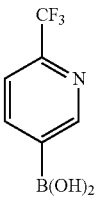 |
| (vi) | 4-(methylsulfonyl)phenyl-boronic acid | 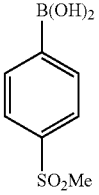 |
| (vi) | 4-(trifluoromethyl)phenyl-boronic acid | 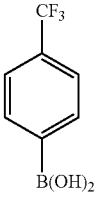 |
| (vi) | 4-carbamoylphenylboronic acid | 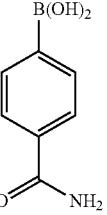 |
| (vi) | 4-(morpholine-4-carbonyl)phenylboronic acid | 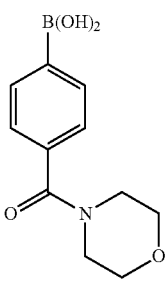 [SMILES: O=C(c1ccc(B(O)O)cc1)N1CCOCC1] |

TABLE 2-continued

| Intermediate's formula | Chemical name | Structure |
|---|---|---|
| (vii) | 5-(4-(methylsulfonyl)phenyl) pyrazin-2-amine | |
| (vii) | 4-(5-aminopyrazin-2-yl) benzamide | |
| (v) | 5-bromo-3-(6-methoxypyridin-3-yl)pyrazin-2-amine | 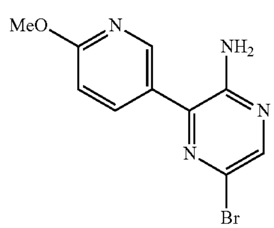 [SMILES: COc1ccc(-c2nc(Br)cnc2N)cn1] |
| (viii) | 3-bromo-5-(4-(methylsulfonyl) phenyl)pyrazin-2-amine | 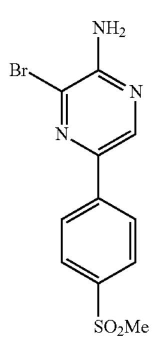 [SMILES: CS(=O)(=O)c1ccc(-c2cnc(N)c(Br)n2)cc1] |

TABLE 2-continued

| Intermediate's formula | Chemical name | Structure |
|---|---|---|
| (viii) | (4-(5-amino-6-bromopyrazin-2-yl)phenyl)(3-hydroxy-pyrrolidin-1-yl)methanone | 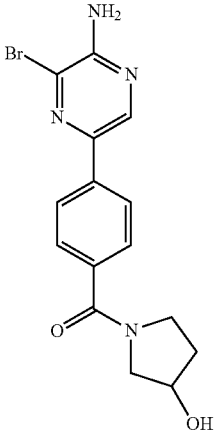 [SMILES: Nc1ncc(-c2ccc(C(=O)N3CCC(O)C3)cc2)nc1Br] |
| (xix) | tert-butyl 4-(4-(5-amino-6-(6-(trifluoromethyl)pyridin-3-yl)pyrazin-2-yl)benzoyl)piperazine-1-carboxylate | 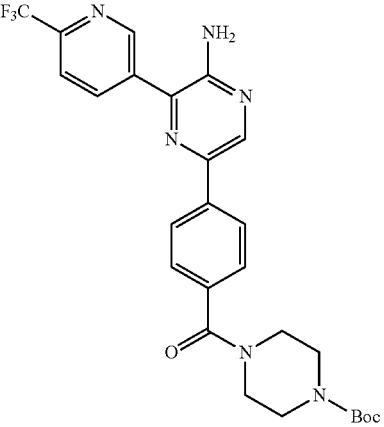 [SMILES: CC(C)(C)OC(=O)N1CCN(C(=O)c2ccc(-c3cnc(N)c(-c4ccc(C(F)(F)F)nc4)n3)cc2)CC1] |
| (xix) | tert-butyl 4-(4-(5-amino-6-(4-(trifluoromethyl)phenyl)pyrazin-2-yl)benzoyl)piperazine-1-carboxylate | 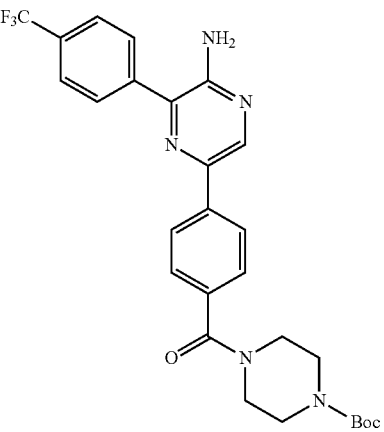 [SMILES: CC(C)(C)OC(=O)N1CCN(C(=O)c2ccc(-c3cnc(N)c(-c4ccc(C(F)(F)F)cc4)n3)cc2)CC1] |

Example 3

Anti-Malarial In Vitro Efficacy of Compounds According to the Invention

The ability of aminopyrazine derivatives according to the invention to kill *P. falciparum* parasites and/or to inhibit its proliferation is tested as follows:

Assay 1:
The protocol used was as described in the supplemental material to Fiddock et al., 2004, *Nature Reviews Drug Discovery*, (3), p 509.

Assay 2:
Compounds are incubated in the presence of 2 or 3% ring stage parasite (*P. falciparum* 3D7 or Dd2) and 0.3% hematocrite in a total assay volume of 50 µl, for 72 hours in a humidified atmosphere at 37° C., 5% $O_2$ and 5% $CO_2$, in Poly-D-lysine coated Cell Carrier Imaging plates (Perkin Elmer). After incubation plates are stained with DAPI (4',6-diamidino-2-phenylindole, Invitrogen) in the presence of Saponin and Triton X-100 (Sigma-Aldrich) and incubated for a further 5 hours at RT in the dark before imaging on the OPERA™ HTS confocal imaging system (Perkin Elmer). The digital images obtained are then analyzed using the PerkinElmer Acapella spot detection software where spots which fulfil the criteria established for a stained parasite are counted. The % inhibition of parasite replication is calculated using DMSO and 2 μM Artemisinin control data.

$EC_{50}$s (ng/ml) are reported in Table 3 below against different strains of P. falciparum K1, NF54 (assay 1).

TABLE 3

| Compound | P. falciparum (K1) $EC_{50}$ ng/mL | P. falciparum (NF54) $EC_{50}$ ng/mL |
|---|---|---|
| 1 | 17 | 16.5 |
| 2 | 4.0 | 4.1 |
| 3 | 4.8 | 6.0 |
| 4 | 4.9 | 5.7 |
| 5 | 5.8 | 7.8 |
| 6 | 3.0 | 3.5 |
| 7 | 4.4 | 4.4 |
| 8 | 2.1 | 2.3 |
| 9 | 4.0 | 4.6 |
| 10 | 4.1 | 3.8 |
| 11 | 3.1 | 2.7 |
| 12 | 4.5 | 6.9 |
| 13 | 18 | 18 |
| 15 | 7.1 | 8.5 |
| 17 | 8.7 | 9.3 |
| 18 | 4.5 | 5 |
| 19 | 7 | 8.3 |
| 20 | 5.5 | 8.2 |
| 21 | 2.9 | 4.1 |
| 22 | 4.0 | 4.5 |
| 23 | 2.2 | 2.4 |
| 24 | 3.1 | 4.3 |
| 25 | 2.6 | 3.1 |
| 26 | 4.3 | 5.9 |
| 27 | 2.2 | 3.2 |
| 28 | 10 | 17 |
| 29 | 4.8 | 8.8 |
| 30 | 5.2 | 8.6 |
| 31 | 7.6 | 8.5 |
| 32 | 2.9 | 4.3 |
| 33 | 5.6 | 8.2 |
| 34 | 4.0 | 4.7 |
| 35 | | 3.2 |
| 36 | | 2.6 |

These data show that aminopyrazine derivatives according to the invention are able to inhibit parasite proliferation in infected human erythrocytes. Activities of compounds of the invention against different strains of P. falciparum as measured by $EC_{50}$ in the above assays are ≤20 ng/mL.

Example 4

Anti-Malarial In Vivo Efficacy of Compounds According to the Invention

The ability of aminopyrazine derivatives according to the invention to show antimalarial efficacy in vivo can be tested by using the protocols described in the supplemental material to Fidock et al., 2004, Nature Reviews Drug Discovery, (3), p 509.

Table 4 below show the percentages of inhibition of parasitemia following 4 daily oral doses.

TABLE 4

| Compound | 3 mg/kg po | 10 mg/kg po |
|---|---|---|
| 2 | 94.0 | 99.9 |
| 3 | 99.9 | 99.9 |
| 4 | 99.9 | 99.9 |
| 5 | 99.4 | 99.9 |
| 6 | 99.9 | 99.9 |
| 7 | 81.0 | 99.8 |
| 8 | 99.9 | 99.9 |
| 11 | 99.9 | 99.9 |
| 12 | 99.9 | |
| 13 | 99.9 | 99.9 |
| 17 | 99.6 | |
| 21 | 99.6 | |
| 23 | 98.7 | |
| 24 | 87.6 | |
| 25 | 90 | |
| 27 | 88 | |
| 35 | 99.9 | 99.9 |
| 36 | 99.9 | 99.9 |

The invention claimed is:

1. An aminopyrazine according to Formula (I),

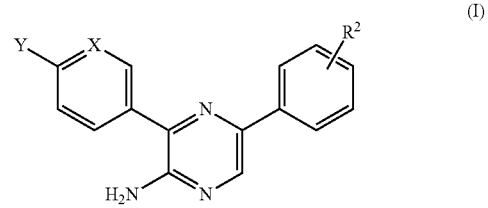

(I)

wherein X is $CR^1$ or N; Y is selected from $CF_3$, —C(O)—$NR^3R^4$; O—$R^6$; $SO_2R^6$; $R^1$ is selected from H and halogen; $R^2$ is selected from $SO_2$—$R^5$ and —C(O)—$R^{10}$; $R^3$ and $R^4$ are independently selected from H and optionally substituted $C_1$-$C_6$ alkyl; $R^5$ is selected from —$NR^7R^8$ and $R^9$; $R^6$ is optionally substituted $C_1$-$C_6$ alkyl; $R^7$ and $R^8$ are independently selected from H and optionally substituted $C_1$-$C_6$ alkyl; $R^9$ is an optionally substituted $C_1$-$C_6$ alkyl; $R^{10}$ is —$NR^{11}R^{12}$; $R^{11}$ and $R^{12}$ are independently selected from H and optionally substituted $C_1$-$C_6$ alkyl or $NR^{11}R^{12}$ form together an optionally substituted heterocycloalkyl; or a pharmaceutically acceptable salt, hydrate, solvate, or polymorph, tautomer, geometrical isomer, or an optically active form thereof.

2. The aminopyrazine according to claim 1, wherein X is N.

3. The aminopyrazine according to claim 1, wherein X is $CR^1$.

4. The aminopyrazine according to claim 1, wherein Y is $CF_3$.

5. The aminopyrazine according to claim 1, wherein Y is —C(O)—$NHR^3$.

6. The aminopyrazine according to claim 1, wherein Y is $SO_2$—$R^6$.

7. The aminopyrazine according to claim 1, wherein $R^2$ is $SO_2$—$R^5$.

8. The aminopyrazine according to claim 1, wherein $R^2$ is $SO_2$—$R^9$.

9. The aminopyrazine according to claim 1, wherein $R^2$ is $SO_2$—$R^9$ and $R^9$ is optionally substituted $C_1$-$C_6$ alkyl.

10. The aminopyrazine according to claim 1, wherein $R^2$ is —C(O)—$R^{10}$.

11. The aminopyrazine according to claim 10, wherein $NR^{11}R^{12}$ form together an optionally substituted heterocycloalkyl.

12. The aminopyrazine according to claim 10, wherein $R^{11}$ and $R^{12}$ are independently selected from H and optionally substituted $C_1$-$C_6$ alkyl.

13. The aminopyrazine according to claim 1, wherein the aminopyrazine is selected from the following group:
- 3-(6-methoxypyridin-3-yl)-5-(4-(methylsulfonyl)phenyl) pyrazin-2-amine;
- 5-(4-(methylsulfonyl)phenyl)-3-(4-(trifluoromethyl)phenyl)pyrazin-2-amine;
- 5-(4-(methylsulfonyl)phenyl)-3-(6-(trifluoromethyl)pyridin-3-yl)pyrazin-2-amine;
- 4-(5-amino-6-(4-(trifluoromethyl)phenyl)pyrazin-2-yl) benzamide;
- 4-(5-amino-6-(6-(trifluoromethyl)pyridin-3-yl)pyrazin-2-yl)benzamide;
- (4-(5-amino-6-(4-(trifluoromethyl)phenyl)pyrazin-2-yl) phenyl)(4-methylpiperazin-1-yl)methanone;
- (4-(5-amino-6-(6-(trifluoromethyl)pyridin-3-yl)pyrazin-2-yl)phenyl)(4-methylpiperazin-1-yl)methanone;
- (4-(5-amino-6-(4-(trifluoromethyl)phenyl)pyrazin-2-yl) phenyl)(piperazin-1-yl) methanone;
- (4-(5-amino-6-(6-(trifluoromethyl)pyridin-3-yl)pyrazin-2-yl)phenyl)(piperazin-1-yl) methanone;
- (4-(5-amino-6-(6-(trifluoromethyl)pyridin-3-yl)pyrazin-2-yl)phenyl)(morpholino) methanone;
- (4-(5-amino-6-(4-(trifluoromethyl)phenyl)pyrazin-2-yl) phenyl)(morpholino)methanone;
- (4-(5-amino-6-(6-(trifluoromethyl)pyridin-3-yl)pyrazin-2-yl)phenyl)(4-methyl-1,4-diazepan-1-yl)methanone;
- 4-(5-amino-6-(3-fluoro-4-(trifluoromethyl)phenyl) pyrazin-2-yl)benzamide;
- 4-(5-amino-6-(4-(methylsulfonyl)phenyl)pyrazin-2-yl) benzamide;
- 4,4'-(3-aminopyrazine-2,6-diyl)dibenzamide;
- 4-(3-amino-6-(4-carbamoylphenyl)pyrazin-2-yl)-N-methylbenzamide;
- 4-(5-amino-6-(6-(trifluoromethyl)pyridin-3-yl)pyrazin-2-yl)-N-methylbenzene sulfonamide;
- 5-(4-(ethylsulfonyl)phenyl)-3-(6-(trifluoromethyl)pyridin-3-yl)pyrazin-2-amine;
- 5-(4-(isopropyl sulfonyl)phenyl)-3-(6-(trifluoromethyl) pyridin-3-yl)pyrazin-2-amine;
- (4-(5-amino-6-(4-(trifluoromethyl)phenyl)pyrazin-2-yl) phenyl)(4-(tert-butyl)piperazin-1-yl)methanone;
- (4-(5-amino-6-(4-(trifluoromethyl)phenyl)pyrazin-2-yl) phenyl)(3-hydroxypyrrolidin-1-yl)methanone;
- (4-(5-amino-6-(6-(trifluoromethyl)pyridin-3-yl)pyrazin-2-yl)phenyl)(4-hydroxy piperidin-1-yl)methanone;
- (4-(5-amino-6-(4-(trifluoromethyl)phenyl)pyrazin-2-yl) phenyl)(4-hydroxypiperidin-1-yl)methanone;
- (4-(5-amino-6-(6-(trifluoromethyl)pyridin-3-yl)pyrazin-2-yl)phenyl)(4-tert-butyl)piperazin-1-yl)methanone;
- (4-(5-amino-6-(4-(trifluoromethyl)phenyl)pyrazin-2-yl) phenyl)(4-methyl-1,4-diazepan-1-yl)methanone;
- (4-(5-amino-6-(6-(trifluoromethyl)pyridin-3-yl)pyrazin-2-yl)phenyl)(1,4-diazepan-1-yl)methanone;
- (4-(5-amino-6-(4-(trifluoromethyl)phenyl)pyrazin-2-yl) phenyl)(1,4-diazepan-1-yl)methanone;
- (4-(5-amino-6-(6-(trifluoromethyl)pyridin-3-yl)pyrazin-2-yl)phenyl)(3-aminopyrrolidin-1-yl)methanone;
- (4-(5-amino-6-(4-(trifluoromethyl)phenyl)pyrazin-2-yl) phenyl)(3-aminopyrrolidin-1-yl)methanone;
- (4-(5-amino-6-(6-(trifluoromethyl)pyridin-3-yl)pyrazin-2-yl)phenyl)(3-hydroxy pyrrolidin-1-yl)methanone;
- (4-(5-amino-6-(6-(trifluoromethyl)pyridin-3-yl)pyrazin-2-yl)phenyl)(4-aminopiperidinyl)methanone;
- (4-(5-amino-6-(4-(trifluoromethyl)phenyl)pyrazin-2-yl) phenyl)(4-aminopiperidinyl)methanone; and
- 5-(4-(cyclopropylmethylsulfonyl)phenyl)-3-(6-(trifluoromethyl)pyridin-3-yl)pyrazin-2-amine;

or a pharmaceutically acceptable salt, hydrate, solvate, or polymorph, tautomer, geometrical isomer, or an optically active form thereof.

14. A pharmaceutical formulation containing at least one aminopyrazine according to claim 1 and a pharmaceutically acceptable carrier, diluent or excipient thereof.

15. The pharmaceutical formulation according to claim 14 further comprising an antimalarial agent.

16. A method for treating malaria in a patient, wherein the method comprises administering an effective amount of an aminopyrazine according to claim 1 in a patient in need thereof.

17. The method according to claim 16, wherein the aminopyrazine is to be administered in combination with an additional antimalarial agent.

18. A process for the preparation of an aminopyrazine derivative according to Formula (I) comprising the step of reacting an intermediate of Formula (v) with a boronic acid of Formula (vi) under Suzuki reaction conditions to lead to a compound of Formula (I):

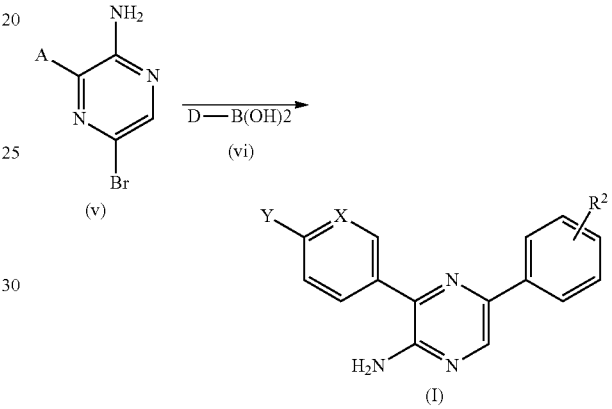

wherein X, Y, and $R^2$ are as defined in claim 1 and A is

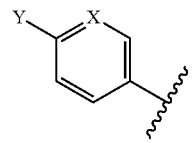

and D is:

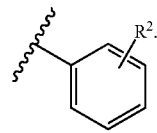

19. A process for the preparation of an aminopyrazine derivative according to Formula (I) comprising the step of reacting a derivative according to Formula (viii) with a boronic acid of Formula (iv) under Suzuki reaction conditions to lead to a compound of Formula (I):

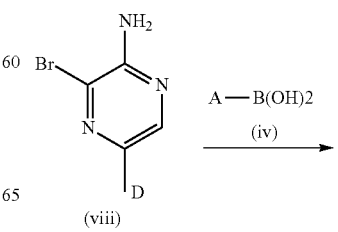

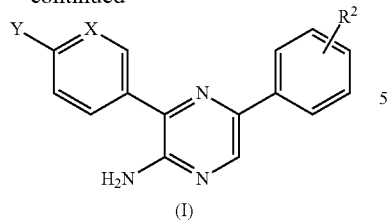
(I)
wherein A, D, X, Y, and R² are as defined in claim 18.
20. A process for the preparation of an aminopyrazine derivative according to Formula (I) comprising the step of reacting a derivative according to Formula (xix) in TFA to lead to a compound of Formula (V):
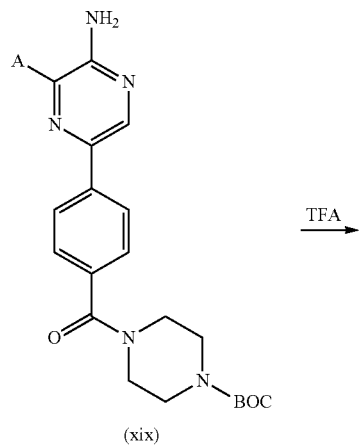
(xix)
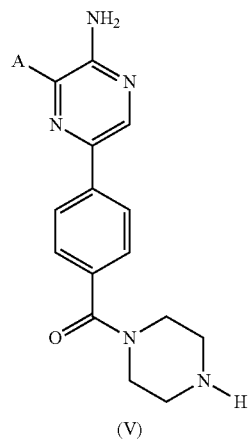
(V)
wherein A is are as defined in claim 18.